US005789682A

United States Patent [19]
Dickinson et al.

[11] Patent Number: 5,789,682
[45] Date of Patent: Aug. 4, 1998

[54] CIRCUIT BOARD ASSEMBLY TORSION TESTER AND METHOD

[75] Inventors: Gerard Truman Dickinson, Owego, N.Y.; James Lee McGinniss, Jr., Friendsville, Pa.; Ronald Francis Tokarz, Maine; Aleksander Zubelewicz, Binghamton, both of N.Y.

[73] Assignee: International Business Machines Corporation, Armonk, N.Y.

[21] Appl. No.: 932,127

[22] Filed: Sep. 17, 1997

Related U.S. Application Data

[63] Continuation of Ser. No. 709,292, Sep. 9, 1996, Pat. No. 5,736,646, which is a continuation of Ser. No. 452,361, May 30, 1995, abandoned, which is a continuation of Ser. No. 208,774, Mar. 9, 1994, Pat. No. 5,567,884.

[51] Int. Cl.$^6$ ............................................. G01N 3/20
[52] U.S. Cl. ............................................. 73/814
[58] Field of Search ............................. 73/841, 851, 853, 73/814, 847, 848, 810, 802; 324/158; 364/508

[56] References Cited

U.S. PATENT DOCUMENTS

| | | |
|---|---|---|
| 3,381,526 | 5/1968 | Rastogi et al. . |
| 3,665,751 | 5/1972 | Paine et al. . |
| 3,910,105 | 10/1975 | Hoffstedt . |
| 4,003,247 | 1/1977 | Moser et al. . |
| 4,567,774 | 2/1986 | Manahan et al. . |
| 4,777,829 | 10/1988 | Fleischman . |
| 4,895,027 | 1/1990 | Manahan, Sr. . |
| 4,958,522 | 9/1990 | McKinlay . |
| 5,079,955 | 1/1992 | Eberhardt . |
| 5,184,517 | 2/1993 | Kelzer . |
| 5,195,384 | 3/1993 | Duesler, Jr. et al. . |
| 5,231,882 | 8/1993 | Bertele et al. . |

FOREIGN PATENT DOCUMENTS 3245660  11/1991  Japan .

1723679  3/1992  U.S.S.R. .

OTHER PUBLICATIONS

ITL SM Tech Feb. 1985. SMC Card Torque Tester:, by Center et al., (Unpublished).

Document Number 9402–019, "Mechanical Deflection System Reference Manual", pp. 1–29, by Zubelewicz et al. (Unpulished).

Document Number 9402–027, "Mechanical Deflection System Test Methodology", pp. 1–16, by Zubelewicz (Unpublished).

*Primary Examiner*—Robert Raevis
*Attorney, Agent, or Firm*—Calfee, Halter & Griswold LLP

[57] ABSTRACT

A mechanical deflection system (MDS) includes a torsion tester for circuit boards which imposes controlled repeatable sheer stress to a test board and components mounted thereon by cyclicly twisting the board about a center line. A self centering twisting clamp holds one edge of the board and a rotating clamp connected to a backlash free motor and servo mechanism, holds the opposite edge with a limited clamping force. A computer regulates the motor to apply either a specified maximum twist angle or maximum torque, and receives signals from an optical meter which measures the angle, and from a load cell which measures the torque. The computer is connected to detect failures by measuring the electrical resistance of critical joints during testing and it records the location and number of cycles for each failure. The MDS includes a test method which continues until a large number of fatigue failures have occurred, then the locations and cycles till failure are compared to the data for a similar circuit board produced by a base attachment process. For attachment process development another process is the base, and for attachment process quality monitoring the same process at earlier times is the base. Then the reliability of the circuit board and/or production process is statistically determined.

12 Claims, 22 Drawing Sheets

| | MDS MEAN LIFE, $N_{50}$ | STANDARD DEVIATION, SIGMA |
|---|---|---|
| REWORK | 797 | 0.771 |
| STANDARD | 1183 | 0.152 |
| LEAD-ON-CHIP | 2677 | 0.183 |

FIG. 12

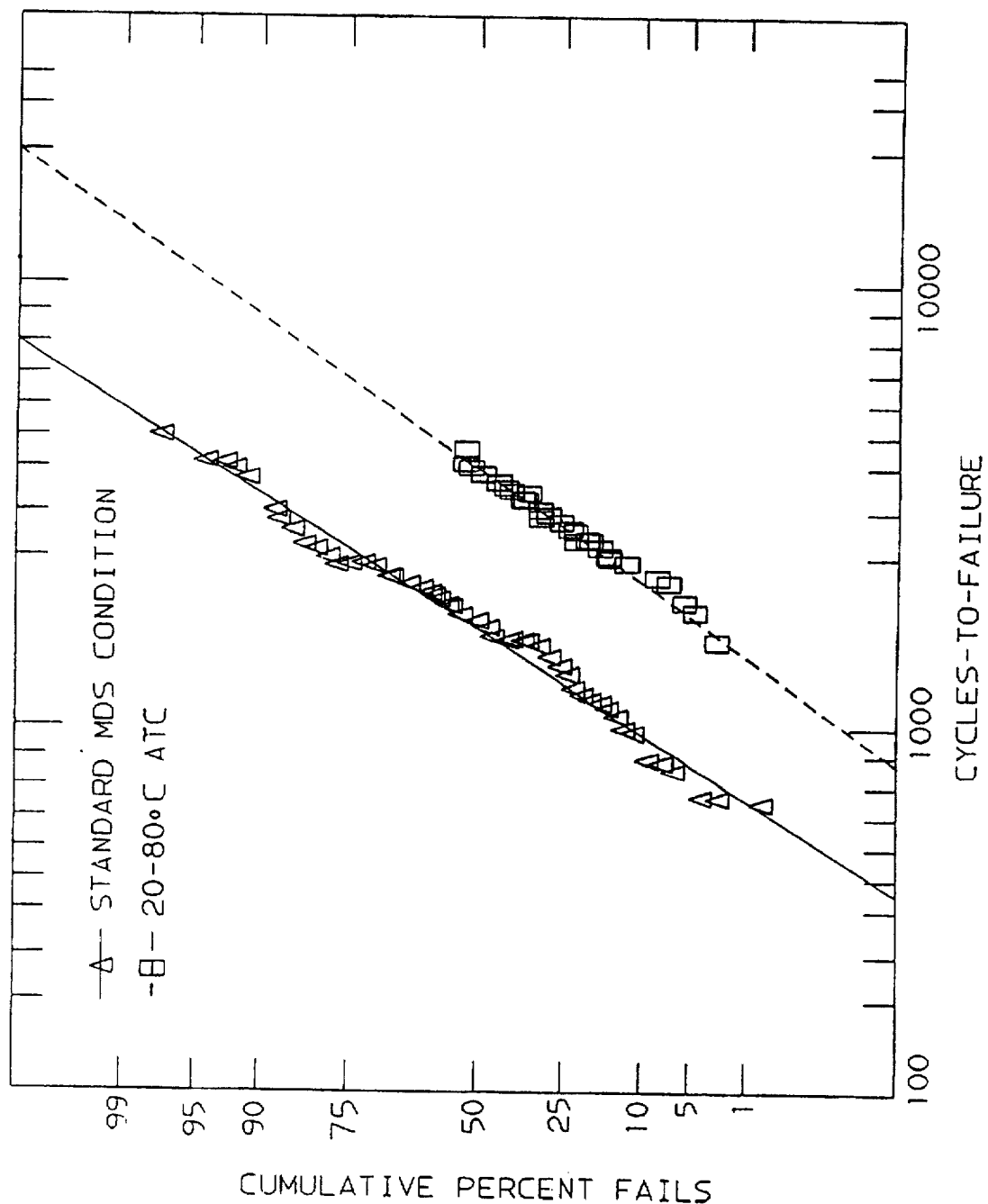

CIRCUIT BOARD ASSEMBLY TORSION TESTER AND METHOD

This application is a continuation of application Ser. No. 08/709,292, filed Sep. 9, 1996 titled "Circuit Board Assembly Torsion Tester and Method", now U.S. Pat. No. 5,736,646, which is a continuation of application Ser. No. 08/452,361 filed May 30, 1995, abandoned, which is a continuation of application Ser. No. 08/208,774 filed Mar. 9, 1994, now U.S. Pat. No. 5,567,884.

FIELD OF INVENTION

This invention is related to methods and apparatus to evaluate the quality of surface mount technology (SMT) electronic assembly processes for circuit board assembly process quality control and/or for-optimizing circuit board assembly processes. More specifically, the invention is related to destructive testing of SMT circuit board assemblies for predicting the reliability of SMT solder joints when exposed to thermal fatigue during operation.

BACKGROUND

Solder joints are a critical element of surface mount attachment of electronic components. Previously, continuous process quality of SMT circuit board assembly was monitored using visual inspection, pull tests, and periodic Accelerated Thermal Cycling (ATC). Visual inspection is not sufficient because many defects are not visually observable. For example, joints of grid array surface mount components can not be readily observed. In pull testing, assembled components are pulled off the circuit board and the appearance of the fractured joints indicate the quality of the assembly process. Again, this method does not disclose all the defects because it does not replicate field failure mechanisms. Both visual inspection and pull testing require the services of a skilled operator for extensive periods of time for each board assembly tested. ATC is a good method of finding defects which could cause field failures. Also, ATC testing can be automated so a skilled operator is only required to electrically test the board after cycling. However, ATC is not a practical testing method for monitoring continuous process quality because the total test time is too long. Typically, ATC data is not available until weeks after production.

Cyclic bending has been used to test the quality of soldered joints in circuit board assemblies. Japanese Patent JP 03-245600 discloses "a test device to check a printed board in soldering quality". The test uses "a probe after the printed circuit board is subjected to a prescribed frequency of bending tests." In Soviet Union patent SU 1723679-A1 constant bending upward and downward is applied to a PCB for "non-destructive quality control testing of metalizations and contact junctions."

Cyclic bending fatigue testing has also been used in other fields for determining bulk fatigue properties of many materials. For example U.S. Pat. No. 3,381,526 to Rastogi et al discloses a method and machine to perform such fatigue tests on cantilever beams with a waist section. Manahan et al in U.S. Pat. No. 4,567,774 discloses "a miniaturized bend test of specimens" and the mechanical behavior of the material is determined from the measurement taken during the "bending of the specimen and is processed according to the principles of linear or non-linear material mechanics;" and in U.S. Pat. No. 4,895,027 discloses a method for determining "plane strain fracture toughness, dynamic plane strane crack initiation and arrest fracture toughness" and other fracture characteristics. U.S. Pat. No. 5,189,517 to Kelzer discloses a "test fixture and test method is designed to establish statistical information concerning the breaking force for deflection of a printed circuit board when the print circuit board is broken along pre-existing score lines." U.S. Pat. No. 5,079,955 to Eberhardt discloses "A fatigue testing system subjects a test specimen to a rotary stress applied about an axis at one or both ends which is perpendicular to the axis of the test selected specimen" and is used to detect "stress failure" for tested materials. U.S. Pat. No. 3,665,751 to Paine discloses "a low-cycle fatigue tester" in which "The specimen" is heated . . . and then deformed cyclically by the two interconnected, exposing, convex jaws of a mandrel driven reciprocally by, an oscillating ram.

Torsional testing has also been used to evaluate mechanical properties of materials and structures. In U.S. Pat. No. 4,958,522 McKinlay discloses a sample "is held between two axially aligned jaws . . . The sample is subjected to a twisting force by rotation of one of the jaws and the force and angle of deflection are measured. This gives a relative determination of the board's structural property and is used to assess damage to the corrugated medium during corrugation and subsequent processing steps such as printing." U.S. Pat. No. 4,003,247 to Moser discloses "In a torsional oscillation apparatus . . . a lower clamp is arranged in a . . . non-rotating manner, and an upper clamp . . . is connected securely to the underside of an oscillatory body suspended from a thread."

All the above citations are hereby incorporated by reference to provide an enbaling disclosure and to support the claims to which applicant is entitled by law.

OBJECTS OF THE INVENTION

The following are some of the objects of this invention.

To develop a method of continuous control of circuit board assembly soldering processes to maintain the quality of solder joint fatigue life.

To provide a measurement of solder joint fatigue life which is closely related to joint fatigue life in actual use.

To provide a method of simulating field fatigue conditions in a test which can be performed sufficiently quick for practical application in process control.

To provide a method of evaluating the failure of soldered joints during simulation tests to determine the quality of joint fatigue life during actual field use.

SUMMARY OF THE INVENTION

The invention of Applicants is a system which includes a testing process and a novel machine for using the process. The system can be used to monitor assembly process quality or to determine the reliability of newly developed assembly processes. The system is known as the Mechanical Deflection System (MDS). The MDS machine includes a torsion tester which imposes controlled repeatable sheer stress to the board and components mounted thereon. The stress produced by the machine is similar to that imposed on components due to thermal cycling of the assembly during field use. The torsion tester includes self-centering fixturing to assure that the circuit board is held in a repeatable position and twisted about the central longitudinal axis of the board.

The fixtures include one stationary clamp and one rotating clamp which is connected to a backlash free motor and servo system. The distance between the clamps can be adjusted to fit various board sizes. The clamps have slips to automatically control the maximum clamping force to prevent board damage resulting in spurious results.

The machine also includes a computer, connected to regulate the motor, and which has apparatus to control the motor for precisely applying either a desired twist angle or a desired torque during the cyclic twisting of the board. An optical meter measures the angle of twist and a torque meter measures the torque applied to the fixturing. The meters generate signals and are connected to transmit the signals to the computer. The circuit board is also connected to the computer to allow electrical resistance of critical joints to be monitored during testing to determine the occurrence of failures. The computer includes apparatus to determine the cycle count at which each failure occurs and the location of the failure. The machine has a data base in which the location and cycle count at which each failure occurs is recorded. The test is continued until a large number of failures is produced. The data base also includes failure cycle and location data for a base process. The base process could be another process for making similar boards or the same process at previous times. The failure cycles and locations of boards produced by a target process are compared to failure cycles and locations of boards produced by the base process. The comparison between the failure locations and cycles are analyzed to statistically determine the reliability of the joints.

Other objects, features and advantages of the invention will be apparent from the detailed description of the invention and the following drawings.

BRIEF DESCRIPTION OF THE DRAWINGS

FIG. 12 shows a summary of the conclusions of the MDS test of FIG. 9.

FIG. 14 is a plot of the normalized distribution of ATC and MDS testing fails.

DETAILED DESCRIPTION OF THE INVENTION

The process of the invention replicates ATC failure mechanisms in a very accelerated manner. The machine of the invention imposes cyclic out-of-plane deformation to an assembled printed circuit board. A portion of the deformation is transferred to SMT solder joints in proportion to the stiffness of the board, rigidity of the electronic components, and compliance of leads and the solder interconnects themselves. The stress magnitude in solder joints is also a function of the component location on the board, the component type, the position of the joint relative to the component, and component to components interactions. The out-of-plane deformation leads to a complex stress system within each individual joint. The methodology disclosed herein was developed through extensive modeling and testing to properly interpret the quality of the assembly. This description will enable those skilled in the art to define the proper test parameters to use the process and equipment described for quick and accurate assembly process quality verification and/or assembly process optimization.

MDS testing can be conducted in a number of different ways, and the those skilled in the art may develop their own approach. However, it is preferred that the logical path illustrated in FIG. 1 be maintained.

Figure 1:
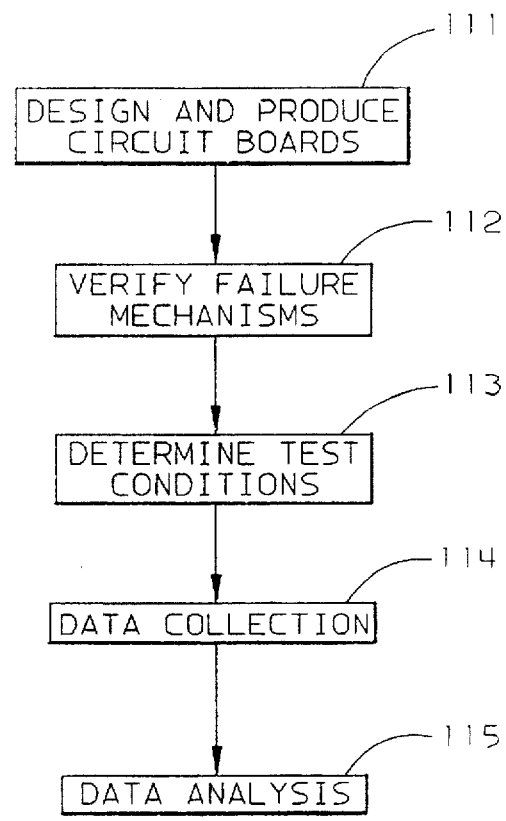
FIG. 1 is a specific embodiment of the invention.

In FIG. 1, step 111 the circuit boards used for testing are designed, debugged, tested, and produced. The test of this invention may be carried out using product assemblies selected from those normally produced on the target process, but preferably, custom designed test assemblies, which are periodically assembled in the same target process as the product assemblies, are used. The test assemblies would mimic the functional product assemblies but provide for automatic generation of failure data. Alternately, both approaches may be used in combination. For example, special test cards may be used to develop and optimize an assembly process and to produce an experience base, and then actual production cards can be tested and analyzed for continuous process quality control.

MDS testing applies various degrees of stresses to solder joints, depending on component type, component location, and joint position. One can reduce the variation by properly selecting the board and component layout. The preferred ratio of the board length to width is approximately one to two. The shorter ends of the board should be placed in the tester fixture. Complex board geometry might also be considered, but this may require design of a special fixture.

Figure 2:
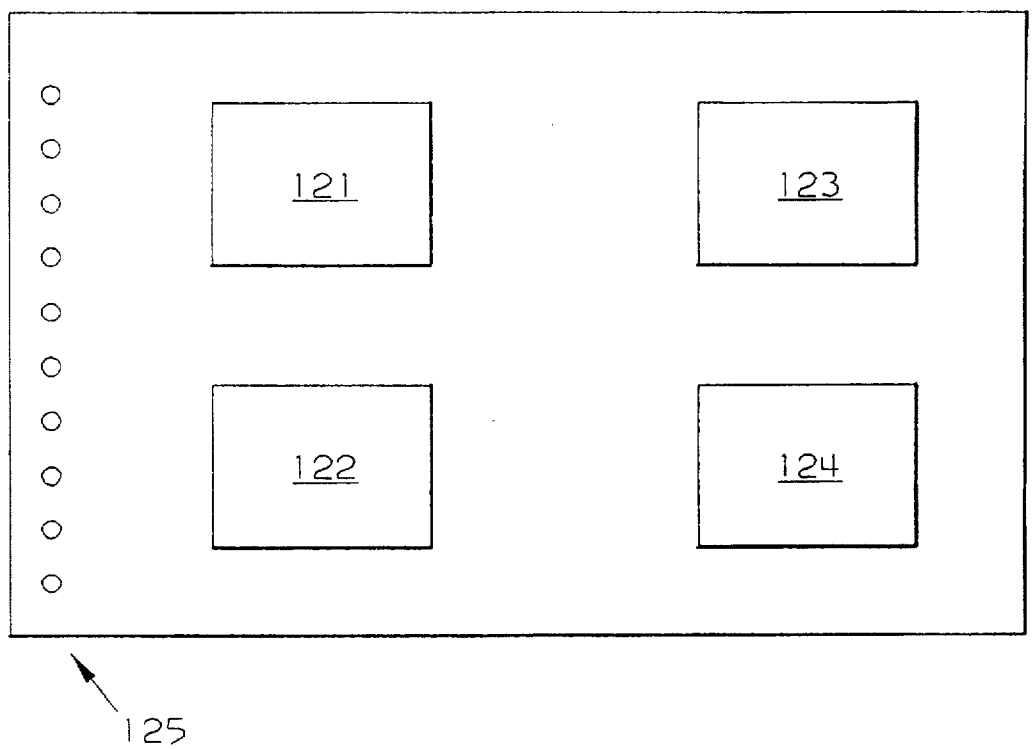
FIG. 2 is an embodiment of the circuit board of the invention showing components mounted symmetrically along the two axis of the board.

As shown in FIG. 2, in the cards used for testing, preferably component locations such as 121, 122, 123, and 124 should be symmetrical with respect to the board axes. Symmetry increases the effective number of data points per board, e.g. if four components are placed symmetrically on a board, then each of the components will experience the same stress in the MDS test, and therefore four equivalent readings will be received from a single board. The proper layout of the components can significantly reduce the number of boards that require testing.

The MDS tester operates at high frequencies (as high a 0.1 Hertz) to achieve a high cycle count in a relatively short time. Visual or periodic electrical assessment can be performed by pausing the test. Preferably, the boards being tested should provide for automatic detection of failures such as connectors for test signals. Preferably, any such connectors should be subject to minimum stress during MDS testing. Therefore, it is recommended that the connectors are parallel to the clamped edges of the card and near the narrow edge of the board which will be inserted in the fixed clamp as shown at 125.

In step 112 failure mechanisms are verified. MDS test results are valid only if the failure mechanisms produced in MDS testing are the same as the failure mechanisms which are produced under the product operating conditions (proper failure mechanisms). Usually the information on failure mechanisms for commonly used technologies is available in industry technical publications. Preferably, potential failure mechanisms are identified and understood prior to running the MDS test. The MDS fracture mechanisms need verification through construction analysis and/or visual joints assessment.

Although the MDS test was developed to replicate joint failure mechanisms, MDS torsion cycles do not exactly mimic product "duty" cycles; therefore, it is possible that the MDS test may not reflect all the factors needed for proper product evaluation, i.e. local thermal mismatches, creep of organic materials. For these reasons failure mechanisms must be verified for proper use of MDS testing.

In step 113, the test conditions are determined. When defining MDS test conditions, two factors are important—first, proper failure mechanisms should be achieved in the minimum test time, and second the amount of data gathered during testing must be sufficient to guarantee adequate assessment of the assembly process. Critical test conditions are the angle of twist, the cycle frequency, and data frequency during testing.

Although testing may be executed using torque control, it is preferable to use deformation (angle of twist) control.

Solder joints receive stress in proportion to the board deformation, therefore the angle of twist is the primary variable that controls the stress magnitude. Also, as the circuit board substrate is fatigued during the test the torque may vary in relation to the angle of twist. The angle of twist is preferably selected between 0.4 degrees and 1.2 degrees per inch of effective length. The effective length of the card is the distance between the MDS clamps. In general, leaded components can be tested at a higher range of deformation (preferably up to 0.9 degrees per inch of length), while leadless components such as Ball Grid Array technology require lower deformation (preferably from 0.4 to 0.6 degrees per inch). Solution of the proper angle of twist is critical. Over-stressed components may exhibit undesired mechanisms of failure, e.g. high lead-tin solders may develop transgranular instead of commonly observed intergranular failure.

For example, field failure reports or ATC testing of Ball Grid Array (BGA) components mounted on a particular circuit board may indicates that the only expected failure mechanism in operation is separation of the balls from the pads. However, during MDS setup debugging, the pads and lines separate from the board surface. In such a case the angle of twist should be reduced or the speed of cycling reduced until the identified failure mechanism is obtained. After proper test setup is obtained, such separation may indicate weaknesses of the board design or the assembly process.

As a general rule, the MDS should be conducted at the highest frequency which would allow for replication of the proper assembly failure mechanisms. The typical range of frequencies is in between 0.05 to 0.15 Hz and preferably should not exceed 0.5 Hz.

In all cases, the MDS test conditions need verification before board testing commences to assure that the proper failure mechanisms are achieved in the minimum time on test. Note that the cycle counts per component type and per component location may vary. Some components may fail at very early stages of cycling, while others may experience very long fatigue life. Therefore, MDS test conditions should be optimized in order to provide meaningful information for all assembly processes. Preferably, the mean number of cycles should be:

1,000 Cycles<Recommended Mean Life<20,000 Cycles.

The lower cycle limit assures the correct high fatigue mode of metallurgical failure, while the upper one has a strictly practical meaning, which is that the MDS test duration should not be longer than necessary. In order to predict the optimum test conditions, one can use the following equations $$\Phi_{desired} = \Phi_{pre-tested} \left[ \frac{N_{desired}}{N_{pre-tested}} \right]^r$$

where the factor r may vary between 0.3 and 0.4. In most cases, one can assume that the factor r=⅓. Furthermore, $N_{pre-test}$ and $N_{desired}$ are the pre-test and desired cycles to failure respectively. Also, $\Phi_{pre-test}$ and $\Phi_{desired}$ are the appropriate angles of twist applied to the assembled boards.

Preferably, the first "main" run, after the MDS test conditions are determined, is used to re-verify the MDS test setup.

Figure 3:
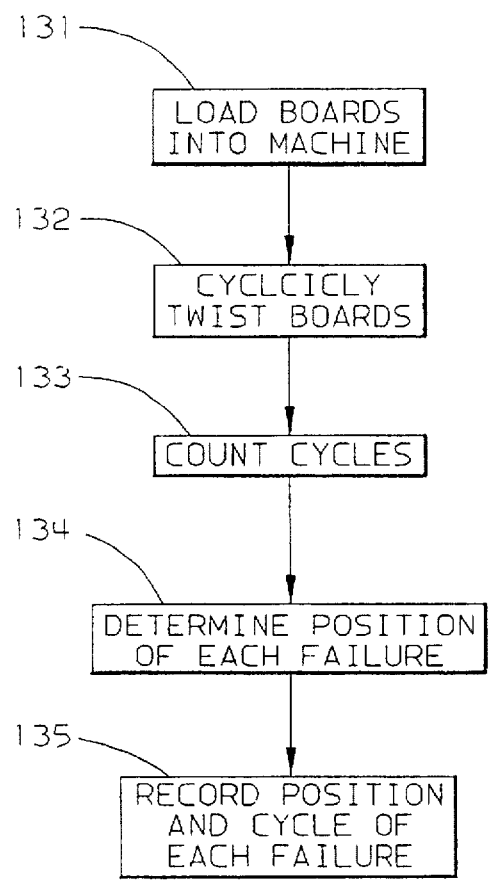
FIG. 3 is a process flow diagram showing a specific embodiment of the process for testing and collecting data of the invention.

In step 114, data are collected during MDS testing. In accordance with the verified test procedure as shown in step 131 of FIG. 3, the card is clamped into the MDS test machine, and in step 132 is twisted at predetermined twist angles at predetermined frequencies for a predetermined number of cycles. In step 133, the number of cycles is counted during the test, and in step 134, the position of each detected failure is determined. In step 135, for each such failure, the cycle number and failure position (the specific joint) is recorded for later analysis. Preferably, the circuit card is connected to a computer system in order to automatically count cycles, determine failure locations, and log each failure with associated cycle count and location in a data base for later statistical analysis performed on the same computer system. If this is not possible, the electrical reading or visual assessments must be gathered at a sufficient frequency during the test in order to provide meaningful statistical analysis.

In step 115 the joint failure data gathered during testing are analyzed. The most critical element of the MDS test methodology is the analysis of the joint failure data collected during testing. The factors that influence the joint fatigue life during testing are as follows:

technology type, (TSOP, BGA, PLCC, . . . );

board flexural stiffness;

component and the interconnect compliances;

component location on the tested board;

component to components interactions.

Each of these factors alters the joint fatigue life during MDS testing. This requires a special algorithm for data analysis of MDS test results.

Figure 4:
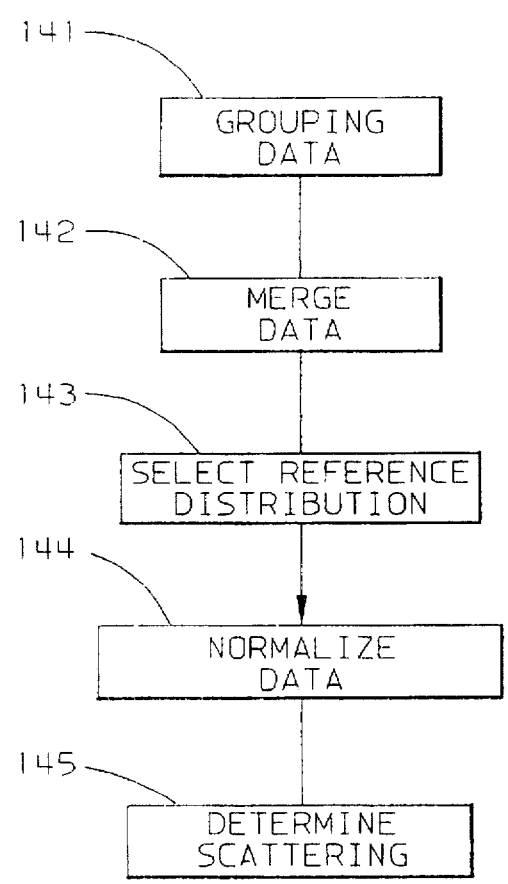
FIG. 4 is a process flow diagram showing the process steps of the statistical analysis of the invention.

FIG. 4 shows the steps for performing the statistical analysis of the invention. In step 141, fatigue data is grouped according to component type, joint location within the tested components, and location of the component on the tested board. The MDS test should provide enough data to build a fails distribution for each selected variable. In step 142 we attempt to merge data. Some of the distributions can be merged together, especially those which belong to the same technology. It is especially convenient if components of the same technology occupy positions which are symmetrical with respect to the axis about which the circuit board is twisted. Since the stress may vary from joint to joint, the fatigue life will vary as well.

Distributions of fails are characterized by the mean cyclic life and the scattering of the data. Thus, the individual distributions of fails can be normalized to some reference. In step 143 a reference distribution is selected for such normalization. Although; there is no special rule for selecting the reference distribution, we prefer to choose a distribution which locates itself in between other distributions. In step 144, the mean lives of the distribution of fails is compared to the selected reference distribution, preferably, the correlation factors are calculated as follows:

$$CF_i = \frac{(N_{50})_{ref}}{(N_{50})_i}.$$

Each individual cycle count within the i-th distribution is multiplied by the correlation factor $CF_i$. Then, the corrected cycle counts are equivalent to those in the reference distribution. Once all the individual distributions are normalized and merged to the referenced one, all the fatigue data can be used to build the equivalent distribution (scattering) of fails in step 145. The equivalent distribution of fails characterizes the quality of the solder joints under consideration.

MDS testing can be used for two basic applications. First MDS can be used as a self-learning monitor of assembly process quality. Second MDS can be used in combination with ATC testing to assess the reliability of new technologies. The scattering of fails and the mean fatigue life define the quality of an assembly process. The scattering of fails alone might provide a sufficient quality measure for assembly processes monitoring. However, development of new technologies require an understanding of the mean fatigue life expectancy of the assembly. In such a case, ATC testing can be conducted in parallel with MDS test in order to verify failure mechanisms and establish bridge between ATC and MDS cycles.

Figure 5:
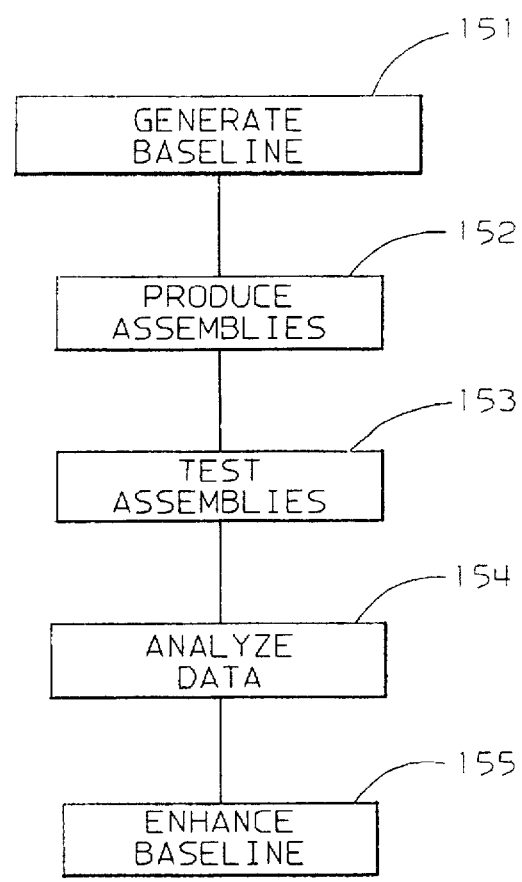
FIG. 5 is a process flow diagram showing the process steps of using the MDS system as a monitor of assembly processes.

FIG. 5 illustrates the process of using the MDS system as a monitor of assembly processes. In this mode the MDS system is designed to expose the development of assembly process defects and allows for very fast corrective actions.

In step 151, a baseline reference distribution is generated from the mean MDS life and the fails scattering (distribution) per component type and per component location resulting from previous MDS tests for the same assembly process. Only statistically valid MDS fatigue data gathered for the assembly process during high quality production is used for the baseline. In step 152, test vehicles must be produced in the assembly line or the functional boards must be selected from those normally produced on the assembly line with a frequency which would allow for proper quality control of the line.

In step 153, the assemblies are tested in accordance with verified test procedures previously discussed. In step 154 the data is analyzed as described above in reference to FIG. 4. The baseline established in step 151 is used as a reference distribution. Any observed anomalies (e.g. life shorter than expected unexpected failure mechanism, etc.) would indicate the presence of flaws in the assembly process. In some cases, MDS testing was found more sensitive than ATC testing in detecting assembly defects (such as module tilt, misregistration, etc.). Since MDS test duration is measured in hours, this test is considered as a "near" real time monitor of an assembly line.

The MDS monitor is a self-learning method, by which statistical data gathered periodically and over a long period of time can enhance baseline data and allow for better understanding of the process critical variables. In this way, MDS test methodology can optimize assembly processes. In step 155, if there are no anomalies, then the current fails distribution can be combined into the baseline. Alternately if are identified and process flaws are identified which correlate to the anomalous then the current test can be used to predict specific process flaws from test results. For example, if investigation of an anomalous fails distribution discloses that pads have begun separating from the circuit board during testing, and investigation determines that the cause of pad separation is a contaminated seeding solution, then similar anomalies in fail distributions will immediately indicate that the seeding solution should be checked for contamination.

As a first example, the MDS test method was used to analyze the quality of a TSOP assembly processes. The analysis included three parts: quality of the TSOP assembly process for standard components, quality of the rework process for standard components, and quality of a process for lead-on-chip type of components. In this example, the scattering of cycles to failure provides the basis for the analysis.

Figure 6:
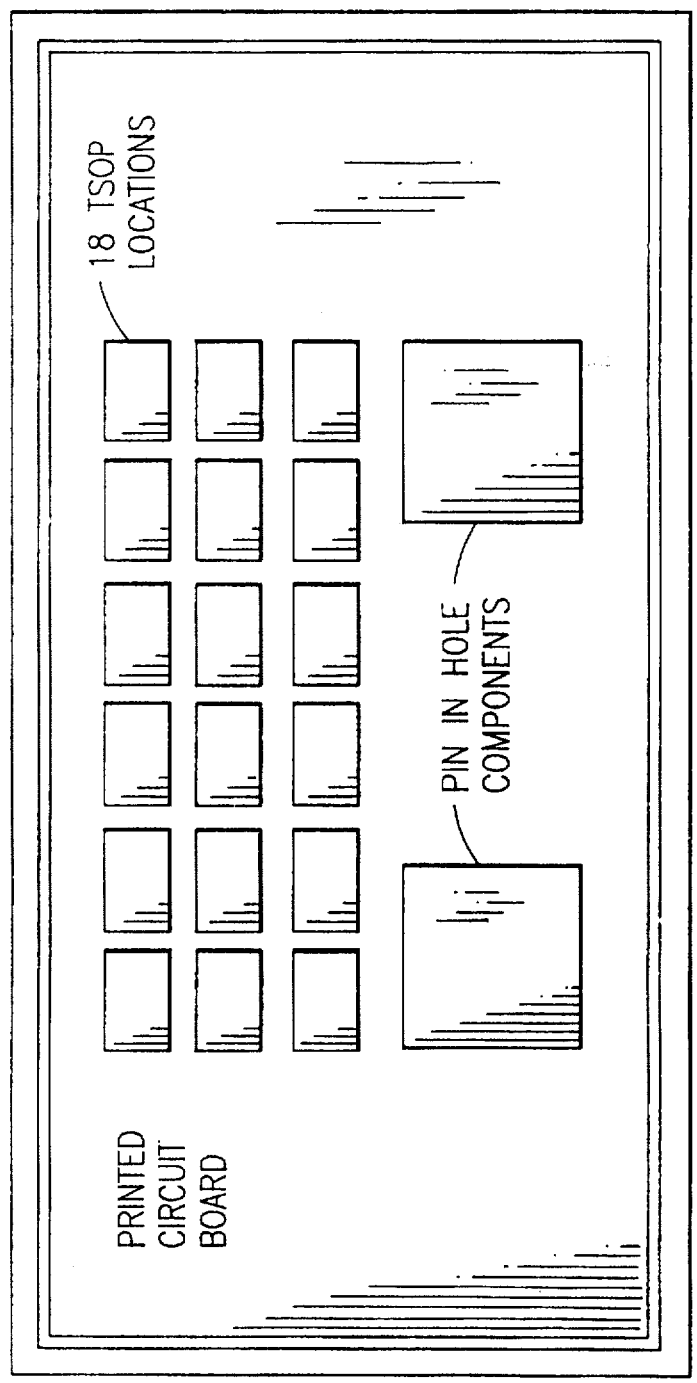
FIG. 6 shows 18 TSOP components assembled to a specific embodiment of the test circuit board of the invention, symmetrically about one axis.
Figure 7B:
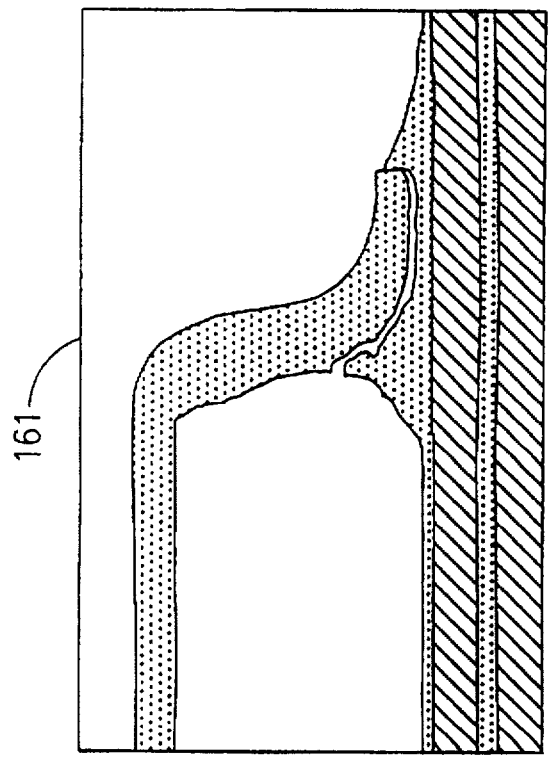
FIGS. 7a and 7b show the leads of lead-on-chip and standard TSOPs attached by a propriety process.
Figure 7A:
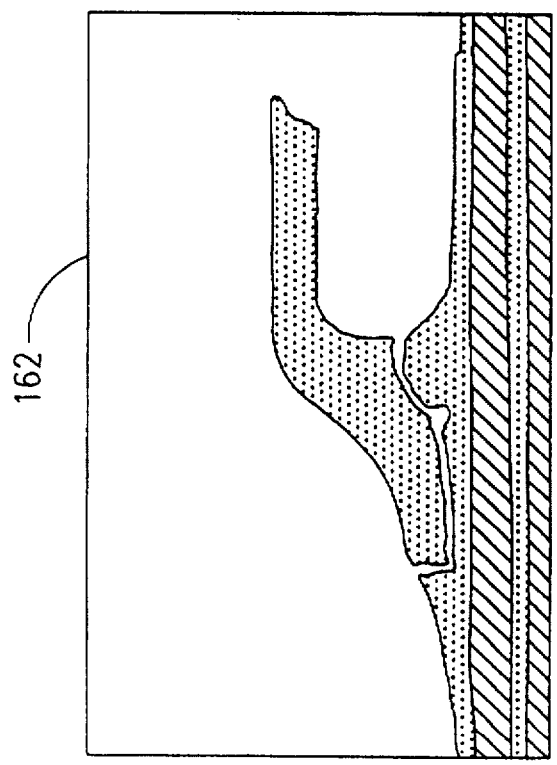

As a first step 111 of FIG. 1, a test vehicle was designed and the TSOP components were assembled to the test vehicle as shown in FIG. 6. The vehicle is a double sided board with 18 TSOP components on each side. The components are placed symmetrically on the board (mirror image of the components with respect to the length of the board as shown on FIG. 6). Both sides are identical. As a result, there are four components in every equivalent location. Each component has all the solder joints stitched (serially connected) together to simplify design and production, so that the MDS fails were counted on a component basis. Eight boards were produced for this test. Boards 1 and 6 have reworked components placed in the locations 4 and 5. Boards 4, 5, and 6 have assembled lead-on-chip components on the top side at all nine locations. The back side of the boards have assembled standard TSOP components. As shown in FIG. 7 lead-on-chip TSOP's 161 have longer and more compliant leads compared with standard TSOP's 162.

Figure 8A:
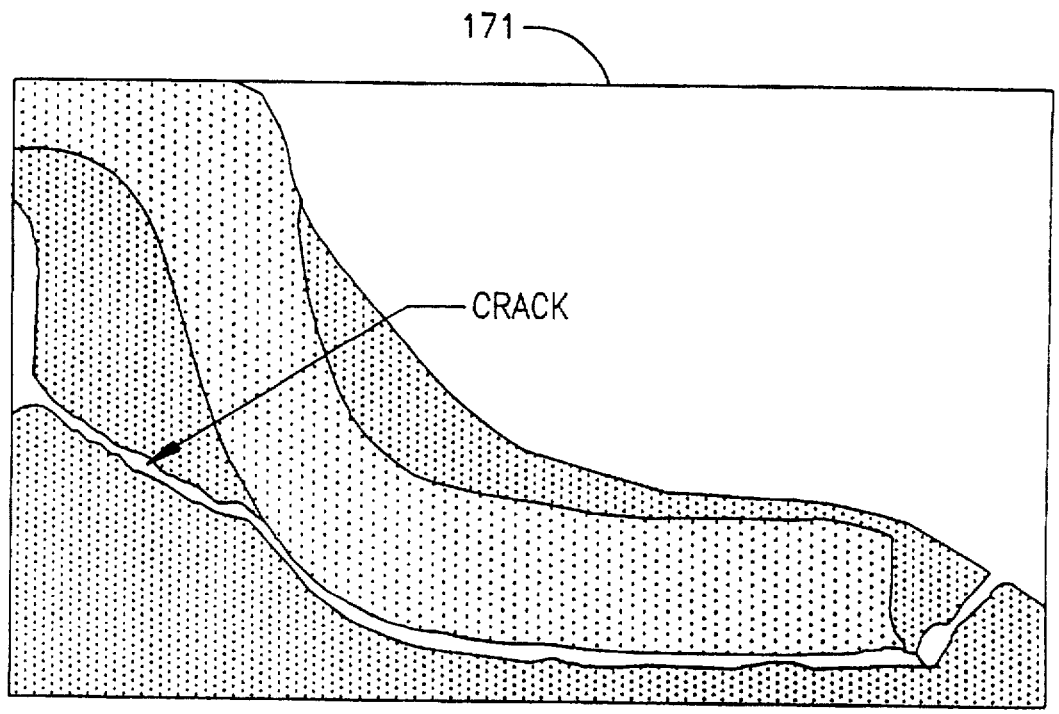
FIGS. 8a and 8b illustrate ATC and MDS testing failures in an example of the process of the invention.
Figure 8B:
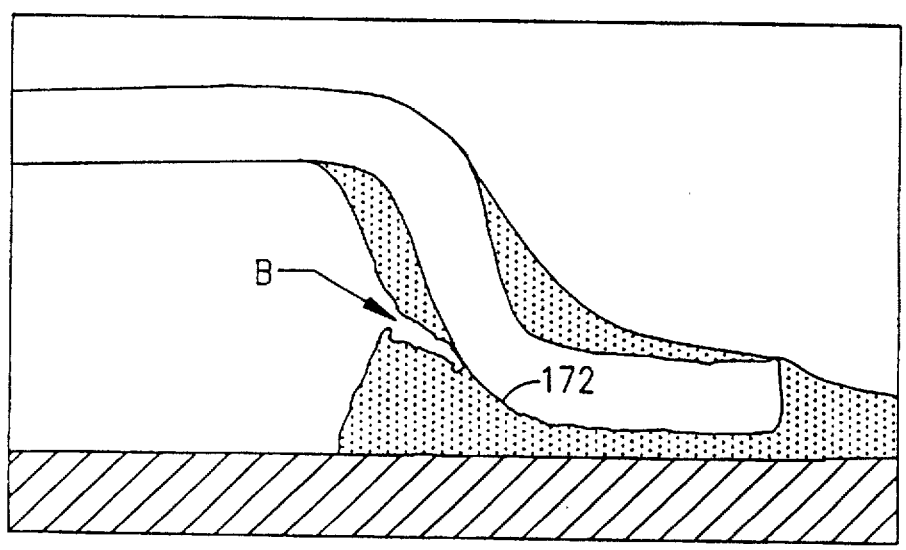

The second step 112 of FIG. 1 is to verify the failure mechanisms. MDS fracture mechanisms must resemble the mechanisms received from ATC testing. Such comparisons were made for TSOP solder joints and it was concluded that the mechanisms are indeed the same. FIG. 8 shows ATC testing failure 171 and MDS testing failure 172 for comparison.

The third step 113 of FIG. 1, test conditions are determined. Initially, a single setup card was used to identify proper test conditions. The angle of twist was set at 0.9 degrees per inch of the card length. The results indicated that the test could be conducted at higher stress levels for reducing the excessive cycle count to failure. Therefore, the angle of twist was set at 1.2 degrees per inch of the effective card length.

Figure 9:
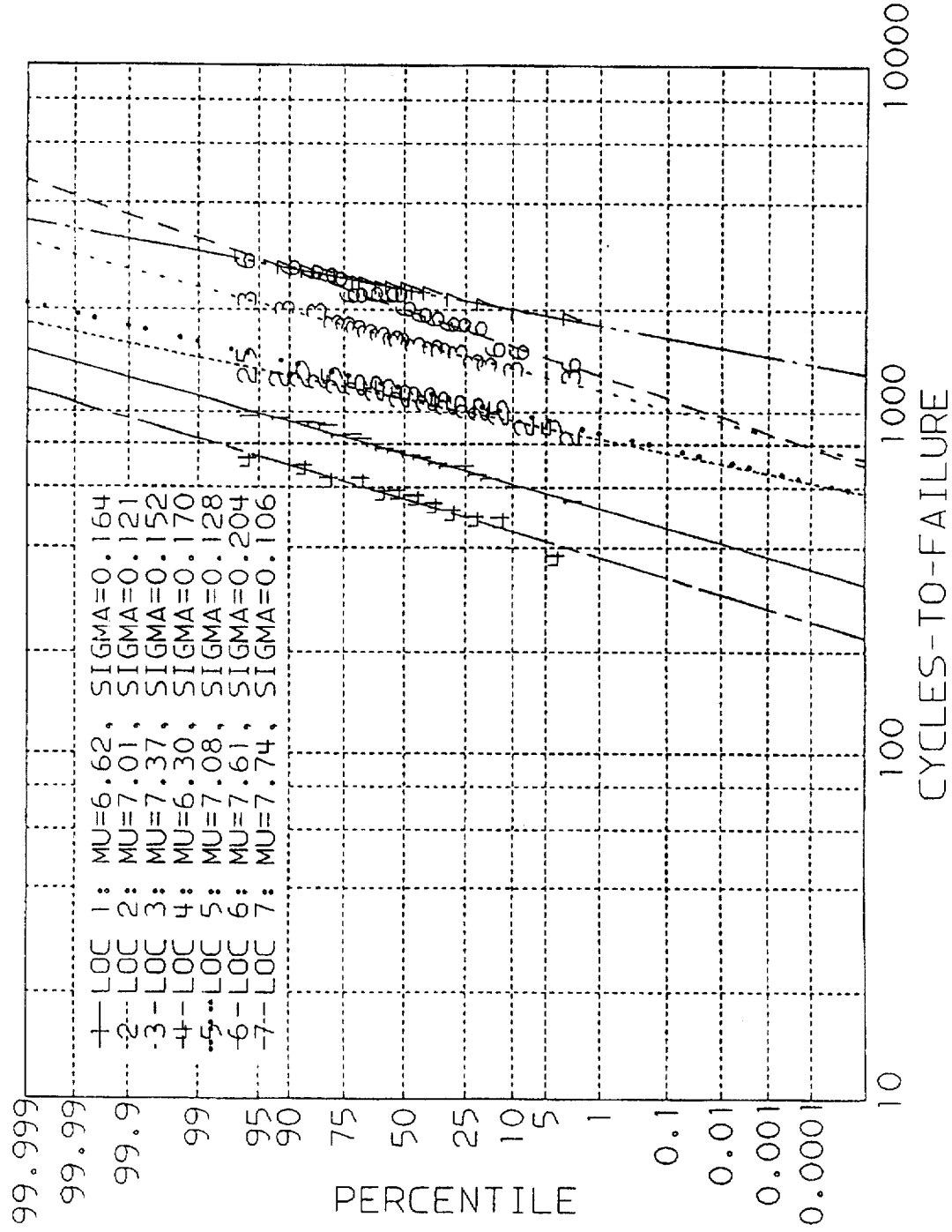
FIG. 9 is a plot of MDS fatigue results in terms of distribution of fails for each location in the example process of the invention.
Figure 10:
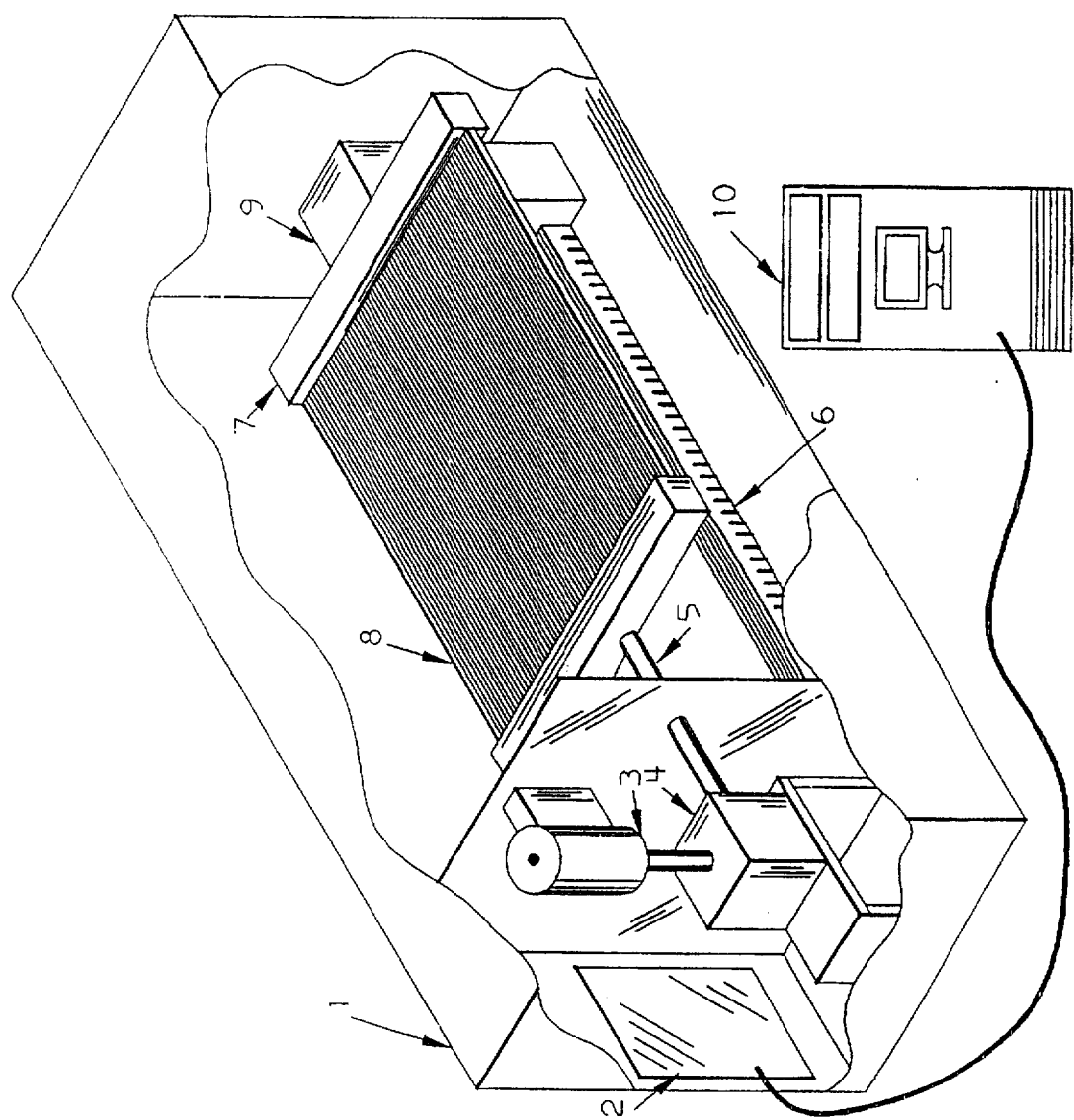
FIG. 10 illustrates an embodiment of an MDS tester of the invention.

The fourth step 114 of FIG. 1, is data collection. Torsion testing commenced and fatigue data were gathered for the first seven equivalent locations. FIG. 9 describes the MDS fatigue results in terms of distribution of fails for each location. The number of fails at locations 8 and 9 was insufficient to build a statistically valid distributions of fails. Note that these distributions are very similar. The distributions can be bridged together to a reference location. In this case, location no. 5 was chosen for that purpose. Subsequently, mean fatigue lives from locations 1, 2, 3, 4, 6, and 7 were compared to the mean life from location number 5. The correlation factors $CF_1$ through $CF_7$ ($CF_i$ was defined above) were used to re-scale the cycle counts from each location. The resulting total number of data points per location number 5 was:

standard components—112,
reworked components—12,
lead-on-chip components—30.

Figure 11:
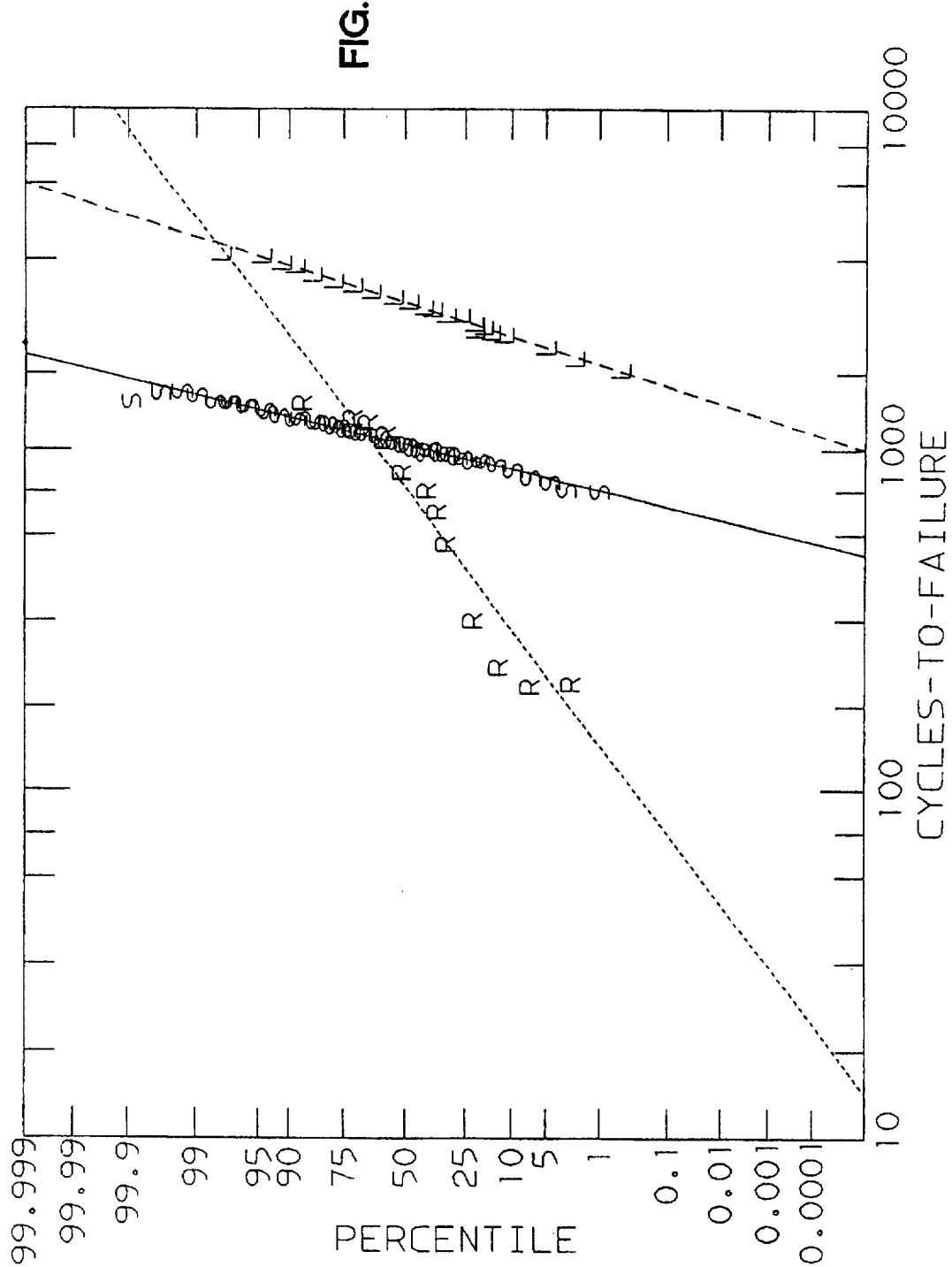
FIG. 11 is a plot of the final distribution of failures in the example of FIG. 9.

The final distributions of fails are presented on FIG. 11, and the conclusions from the test are summarized in FIG. 12.

As a second example, the MDS test method was used to analyze the reliability of a new process to attach chip carrier modules (components) to circuit boards (test vehicles) using a matrix of solder balls herein called Ball Grid Array (BGA).

Figure 13A:
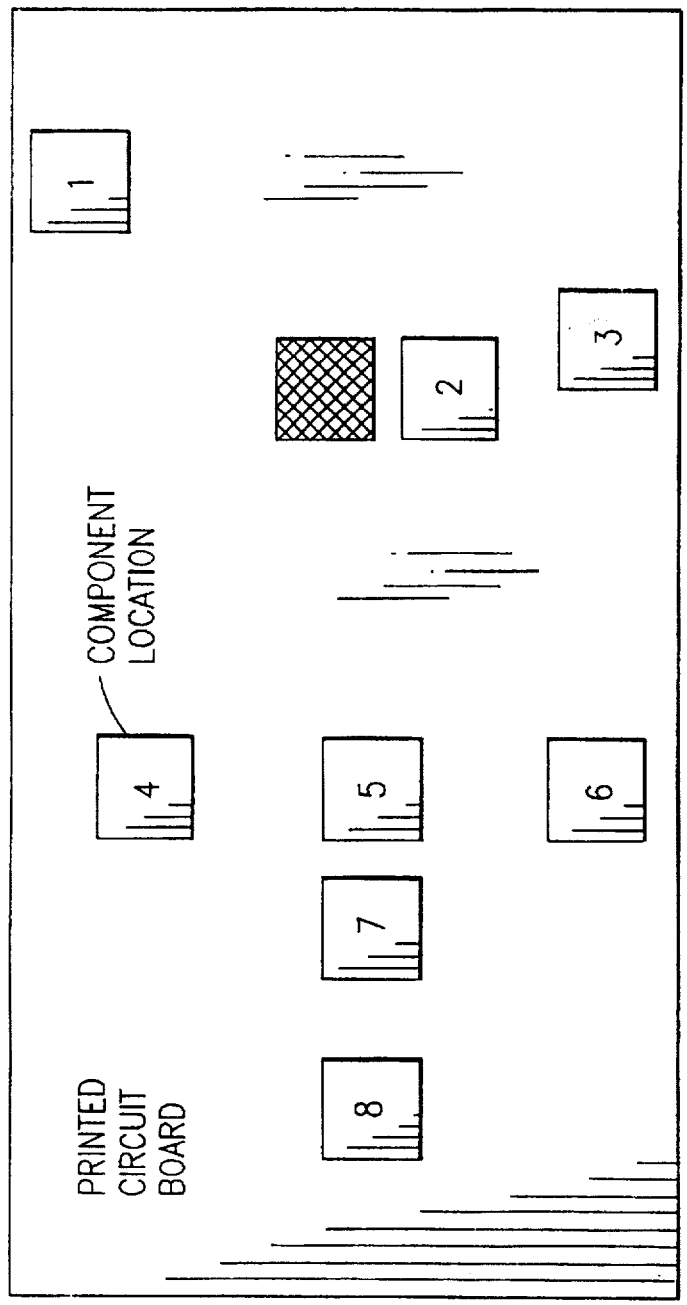
FIG. 13a illustrates another non-symmetrical test vehicle embodiment used in an example embodiment of the MDS process.

As shown in the first step 111 of FIG. 1, test vehicles are designed and produced. Eight BGA components were assembled to a test vehicle, as shown on FIG. 13a. Electrical readings were recorded for each component. There is no symmetry in locations of the components, so that the count of cycles to failure varied from component to component.

As shown in the second step 112 of FIG. 1, failure mechanisms were verified. Normally only one ATC test should be required, but in order to verify the MDS test method statistically, fifteen boards were cycled between the temperatures of 20 and 80 degrees C. with a frequency of 0.00083 Hz to generate multiple failures on the boards. MDS tests were run on three boards using 0.45, 0.6 and 0.9 degrees per inch of the board length and 0.1 HZ frequency.

0.9 degrees per inch caused partial separation of copper pads from tested boards which is not a valid mechanism since the ATC tested boards did not fail by that mechanism.

Figure 13C:
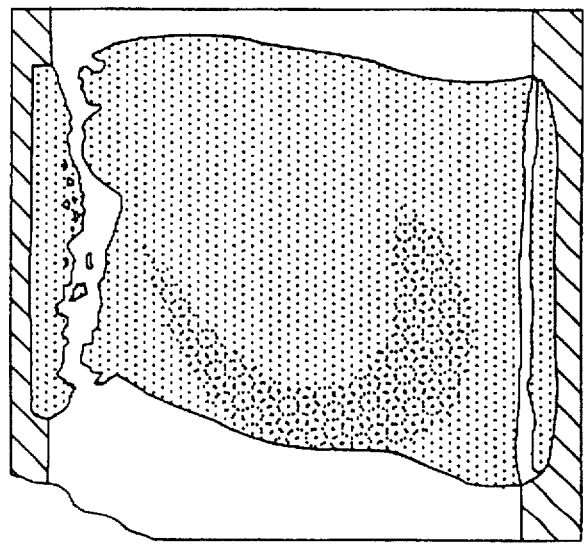
FIG. 13c illustrates a failure produced by MDS testing at a location corresponding to that in 13b, showing a similar failure mechanism.
Figure 13B:
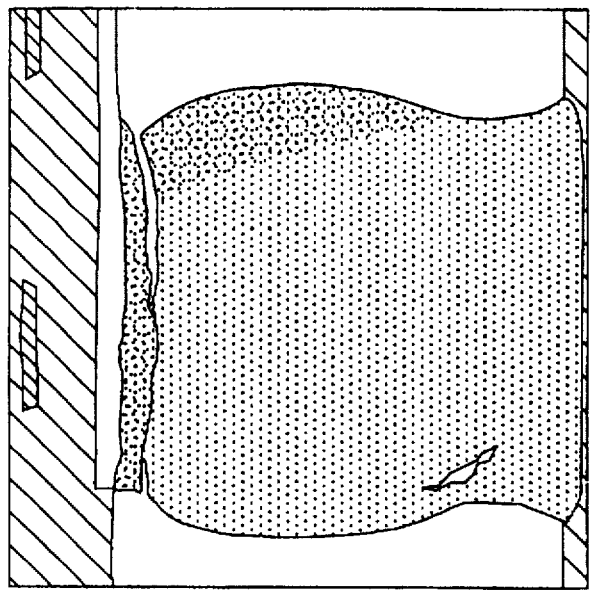
FIG. 13b shows a failure produced by ATC testing.

Comparison of ATC testing as shown in FIG. 13b with MDS failures at 0.6 degrees per inch as shown in FIG. 13c shows that failure mechanisms are similar.

As shown in the third step 113 of FIG. 1, test procedures were determined. The first test runs indicated that both 0.6 and 0.45 degrees per inch were satisfactory in terms of failure mechanisms; however, the time required for testing at 0.45 degrees per inch was excessive, thus 0.6 inches per inch of board length was selected for further tests. In the forth step 114 of FIG. 1, data was collected for an additional 12 cards using the predetermined test procedure and failure data (the cycle and location of each failure) was collected.

The final step 115 in FIG. 1 is statistical analysis of data. The normalized distributions of fails were plotted for MDS and ATC test conditions in FIG. 14. The individual distributions of fails were normalized using Finite Element Analysis and predictive fatigue models. The normalized MDS and ATC plots look almost identical. The only difference is in the test duration. The ATC test would require more than half a year to achieve 100 percent failed components, while the MDS test needed only 16 hours to generate a complete distribution of fails.

The MDS testing methodology requires highly accurate repeatable test parameters. The novel combination of features provided in the MDS torsion test machine provides the accuracy and repeatability required and automatic features for convenience and to prevent errors during testing.

Figure 15:
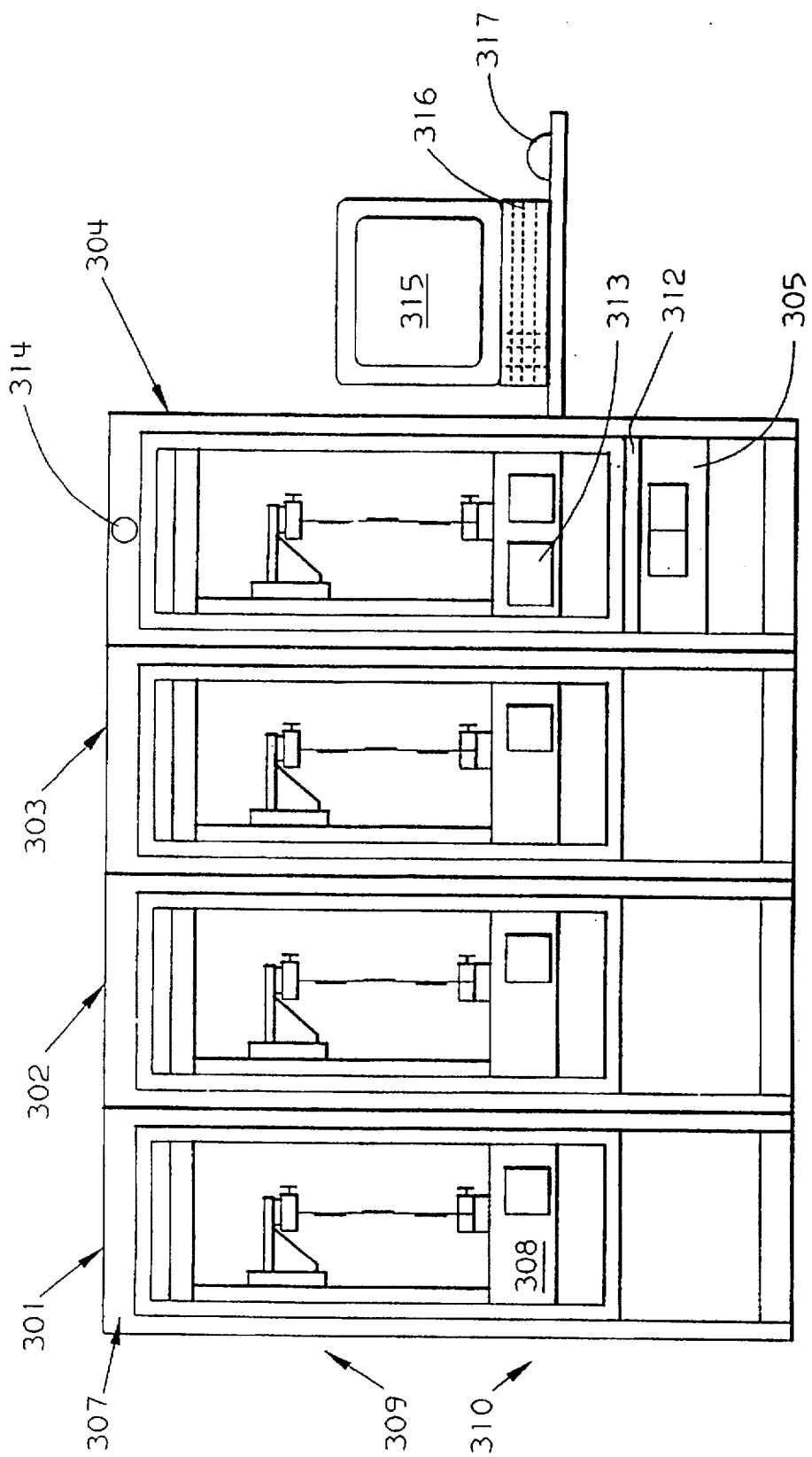
FIG. 15 shows another embodiment of the MDS tester of the invention, including four rest stations.

As shown schematically in FIG. 15, the MDS machine is an assembly of 1 to 4 torsion testing stations 301–304 interconnected with a computer 305 such as an IBM PS/2 7537 (PS/2 is a trade mark of IBM). The test stations each include an industry standard 19 inch rack enclosure 307, an operator panel 308, an upper test section 309 and a lower equipment section 310. Each machine contains a main station 304 in which is mounted the computer and a test circuit monitoring control box 312. The operator panel of the main station contains the power control 313. A big red emergency power off (EPO) button is provided at the top of the main station. The EPO is connected to disconnect all power from every station upon activation. The enclosures may be bolted together as shown to form a unitary machine. A display 315, keyboard 316 and mouse 317 provide the primary user-interface with the computer.

Figure 16:
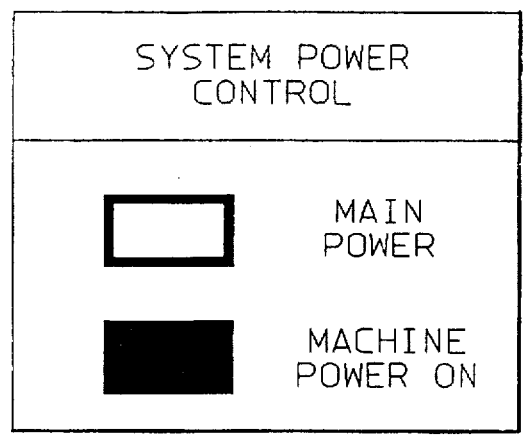
FIG. 16 is an expanded view of the power control area of the operator's panel of the tester of FIG. 15.

FIG. 16 shows an expanded view of power control 313 (see FIG. 16) of the operator's panel for the main station. The power control includes a startup switch 320 (labeled "Machine Power On"), and a power on button 321 (labeled "MAIN POWER").

Figure 17:
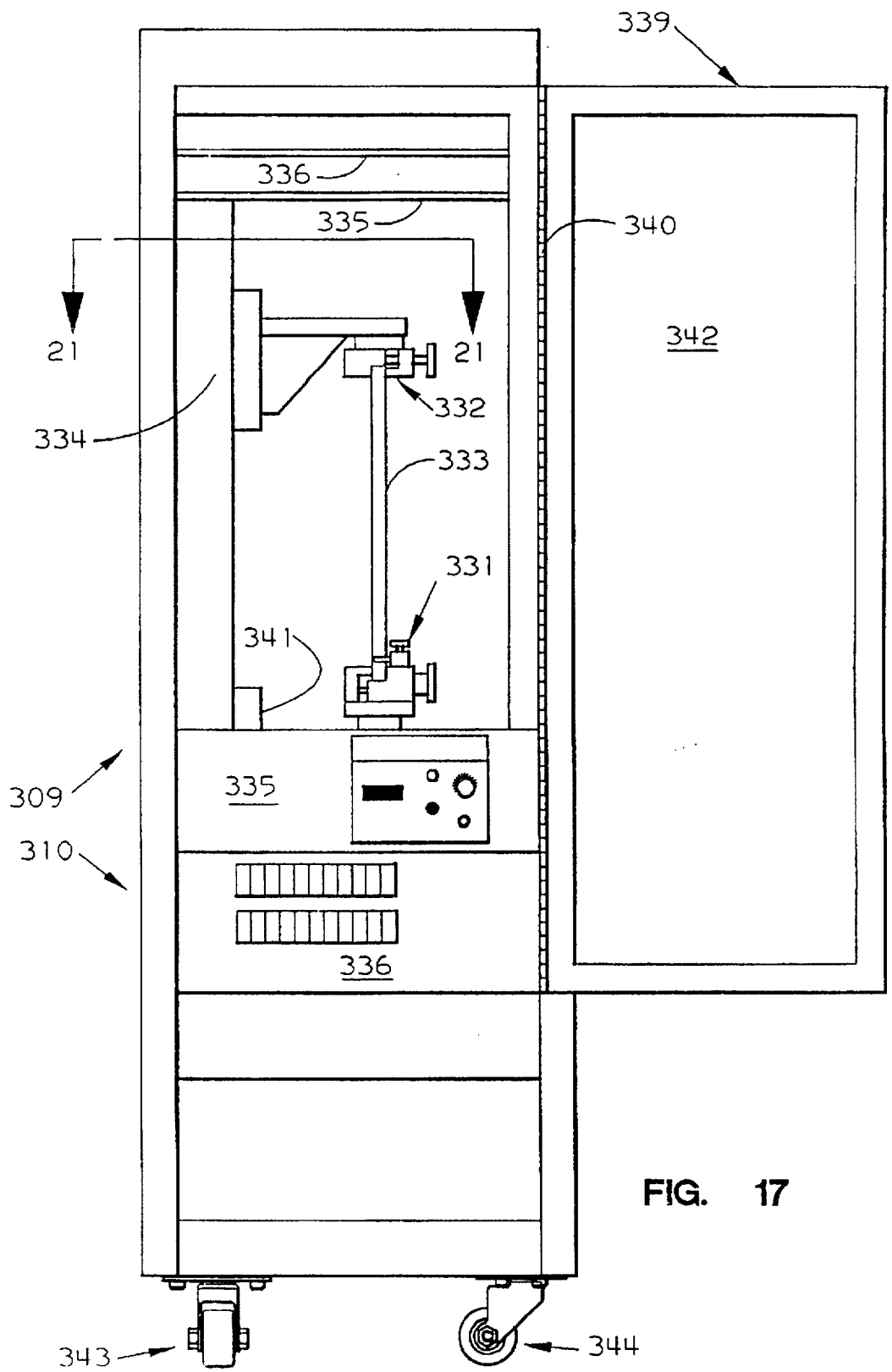
FIG. 17 illustrates one of the stations of the MDS tester of FIG. 15.

FIG. 17 schematically shows a typical station. The test section contains a rotatable lower card clamp 331 and a rotationally fixed upper card clamp 332 for positioning card 333 during torsion testing. The vertical position of the upper clamp is controlled by a linear positioning slide 334. Two stiffener plates 335, 336 minimize twisting of the machine. The lower section 310 is separated from the upper section 309 by a cowling that forms a horizontal bottom wall (not shown), a section 337 that slants toward the front and forms the operator's panel, and a section 338 vertically covering part of the bottom section that can be accessed by removing the cowl. A front door 339 with hinge 340, is opened for loading and unloading test cards. The machine includes an interlock 341 which prevents operation (twisting of the cards) when the door is opened. The door has a central section 342 of clear material (such as polycarbonate)

through which testing may be safely observed. The test station is supported by casters 343, 344 for moving the tester, and the casters can be locked into position for stability.

Figure 18:
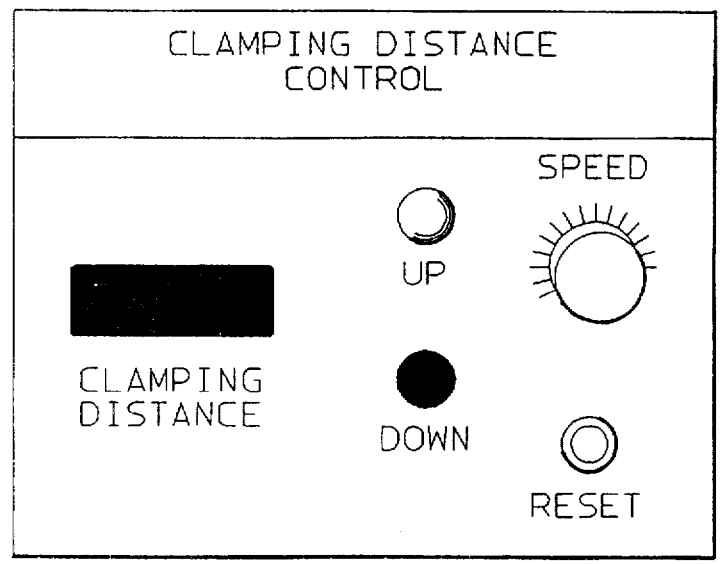
FIG. 18 shows a plan of the clamping distance control panel included in each station of the tester of FIG. 15.

FIG. 18 shows the clamping distance control section of the operator's panel of each test station. Momentary contact push buttons 351, 352 are for moving the upper clamp up and down respectively. Dial 353 controls the speed of the slide motor. A reset 354 is provided. The distance between the clamps is automatically determined as described below and displayed at 355.

Figure 19:
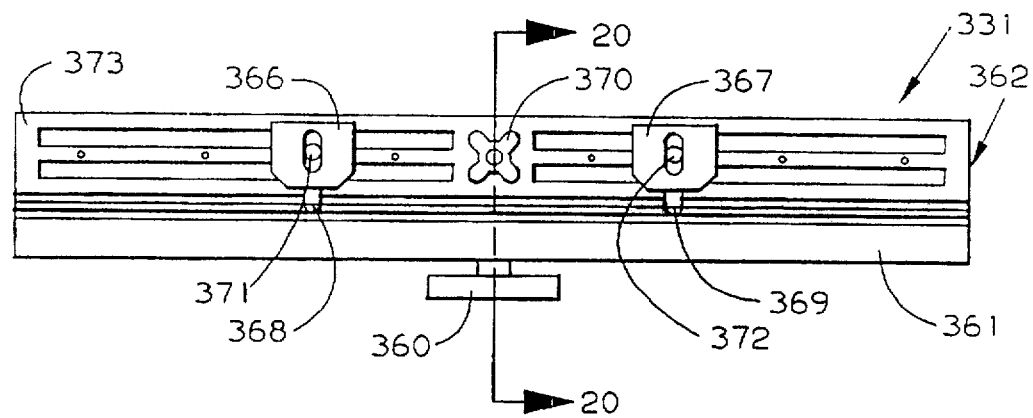
FIG. 19 shows a top view of the lower circuit board clamp of the tester of FIG. 15.
Figure 20:
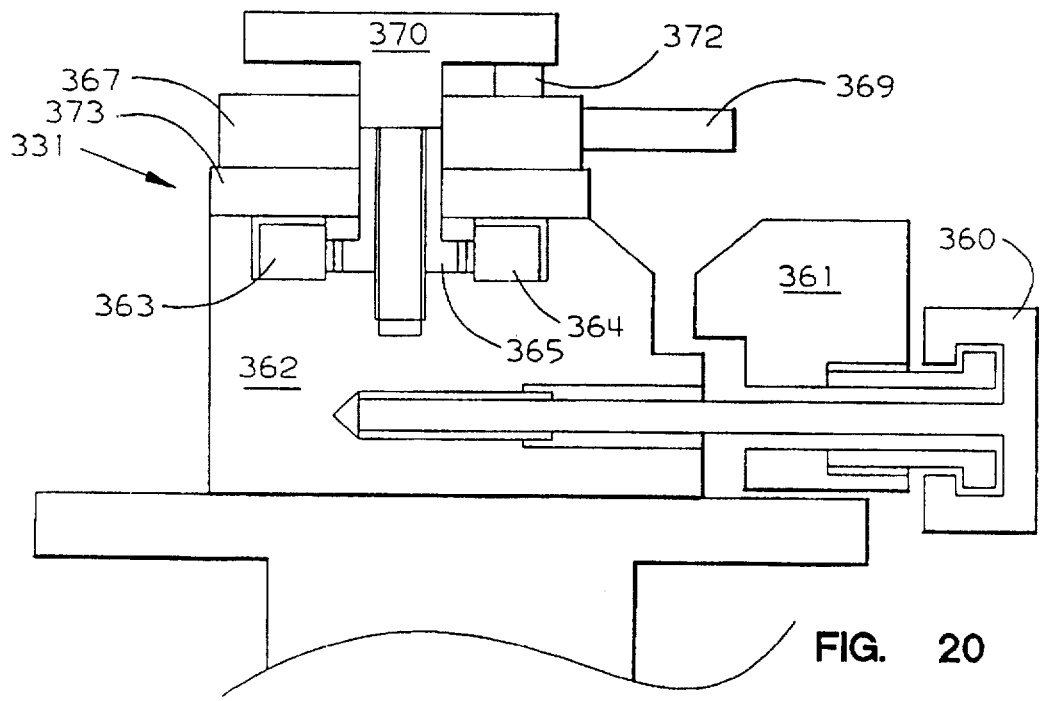
FIG. 20 is a partial sectional view taken through 20—20 of FIG. 19.

FIG. 19 is a top view of lower clamp 331. Clamp knob 360 moves grip 361 horizontally with respect to support 362 to clamp a circuit board (see FIG. 17). Two gear racks 363, 364 positioned in keyways, communicate with pinion gear 365 to move the racks in the longitudinal direction of the clamp, equally and in opposite directions in their respective keyways. Each gear rack is mechanically connected (not shown) to one of the centering slides 366, 367 to move the slides relatively closer or further apart in the longitudinal direction of the clamp. Thus, the distances between the longitudinal center of the clamp and each of the centering slides are always equal.

When a circuit board is loaded into the lower clamp the slides are moved together and the circuit board position is adjusted until both pins 368, 369 are against respective lateral edges of the circuit board. This assures that the circuit board is exactly centered in the lower clamp. Then lock knob 370 is turned to lock the pinion gear and hold the sliders in place. The circuit board can be removed pushing one of the buttons 371, 372 and sliding the board out in its lateral direction. If another board of the same size is loaded it is automatically centered simply by moving one of the pins back, sliding the board laterally into the clamp until board is against the other pin and releasing the pin so that the pins rest against the lateral edges of the board. Cover plate 373 holds the gear racks in the keyways, and provides slots for supporting the centering slides and providing for the movement of the connection between each gear rack and its respective, connected centering slide as the centering slides move closer and further apart.

Figure 21:
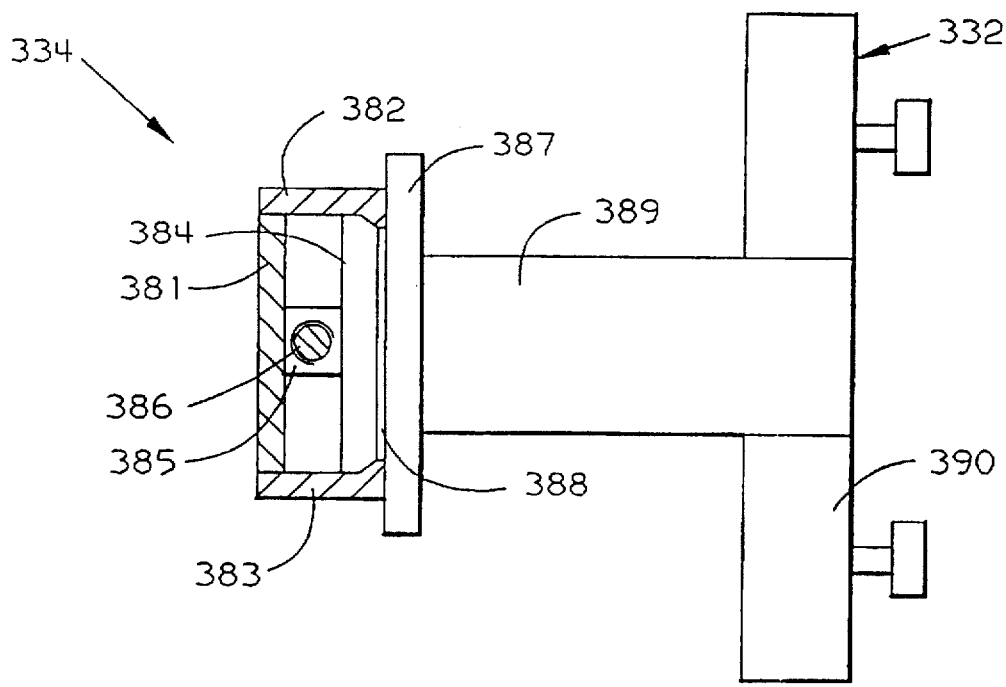
FIG. 21 is a partial section of the upper clamp, screw drive, and slide of the station of FIG. 17.

FIG. 21 is a top view of the upper clamp 332 with a partial section of slide 334. Slide 334 includes back plate 381, and side plates 382, 383. The upper clamp includes an inner sliding plate 384 connected to nut 385 which communicates with a jack screw 386 to selectively position the upper clamp in the vertical direction. The interior sliding plate communicates with an external sliding plate 387 which interact for sliding along slide 334. A spacer plate 388 separates the interior from the exterior sliding plates. The exterior sliding plate supports top support plate 389 which supports a top plate 390 of upper clamp 332.

Figure 22:
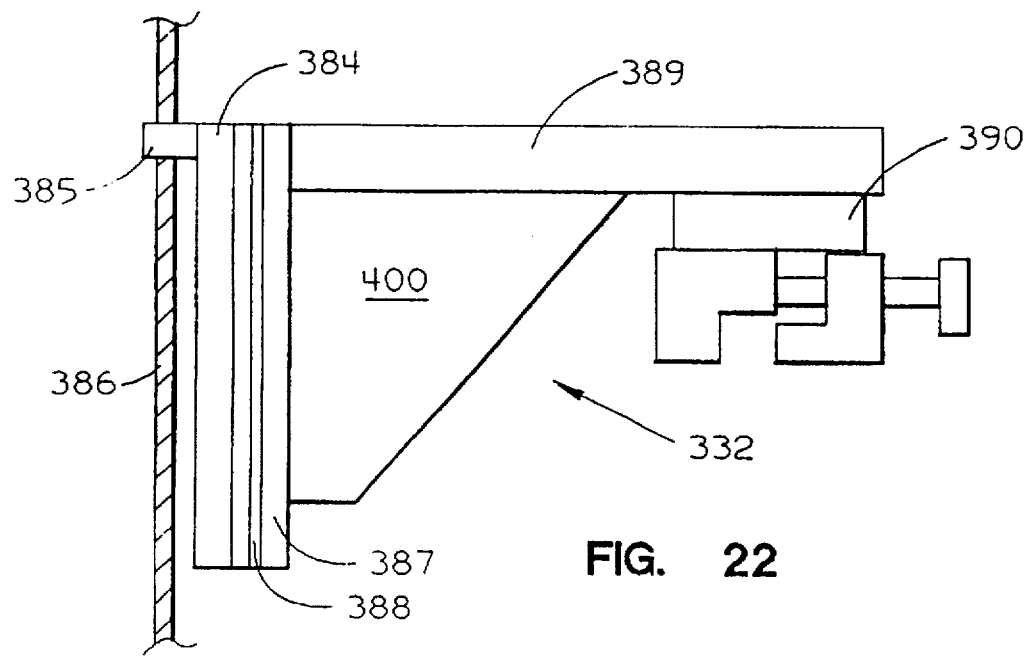
FIG. 22 is an elevation view of the upper clamp of FIG. 21 engaged with the screw drive.

FIG. 22 is a side view of upper clamp 332 with part of jack screw 386 shown. Stiffener plate 400 connects between top plate 389 and outer slide plate 387. Knob 401 moves slide jaw 402 closer/further from fixed jaw 403 to clamp a circuit board for testing.

Figure 23:
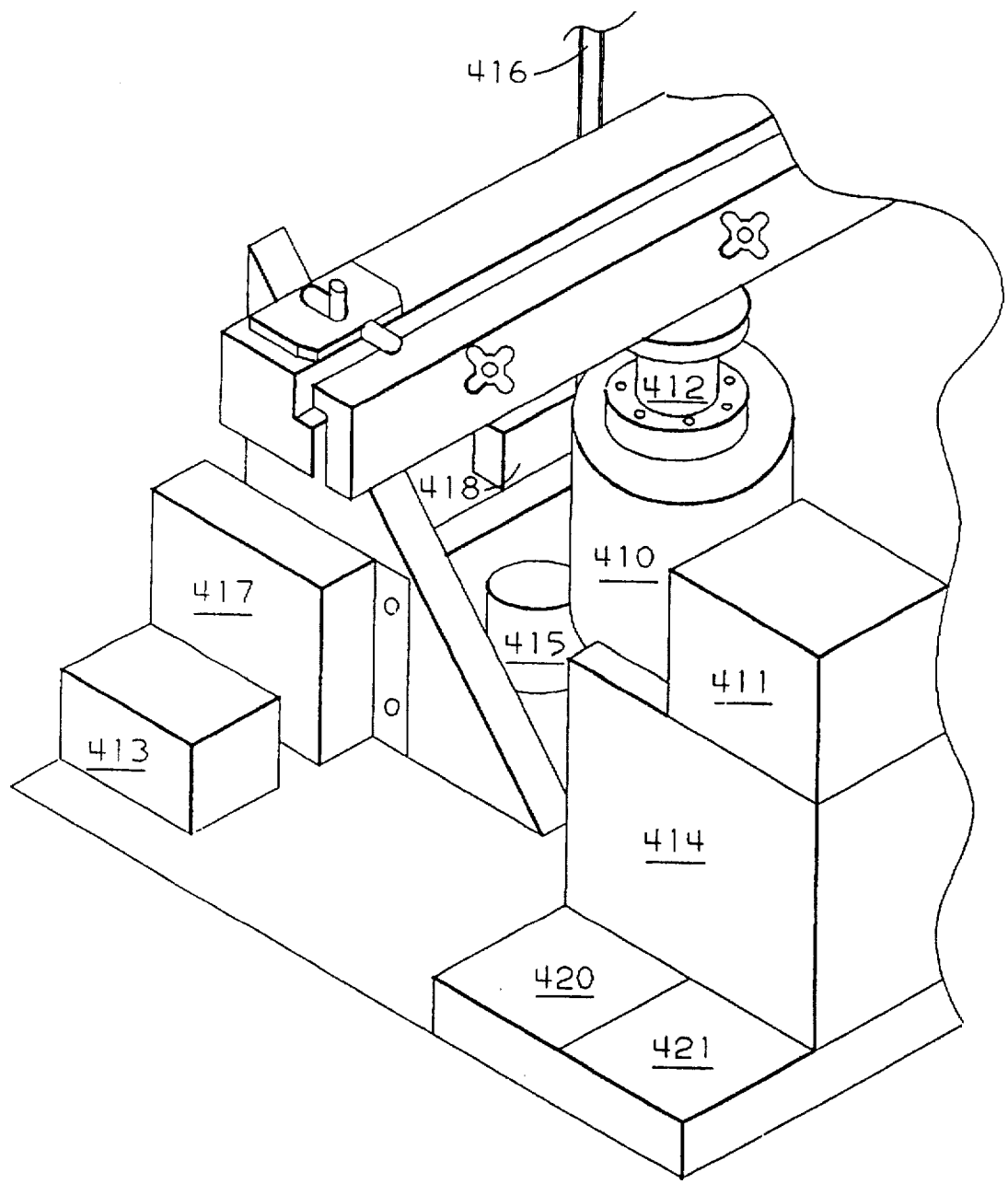
FIG. 23 is an isometric view of a part of the station of FIG. 17 including the lower clamp and drive motors, with the cowling removed.

FIG. 23 is a schematic isometric view of the part of the typical test station of FIG. 17 under the cowling. Servo motor 410 (such as Compumotor Dynaserve™ model DR 1060B (Dynaserve is a trademark of Parker Compumotor, Inc.) is rigidly mounted in the middle of the bottom section of each test station. Motor amplifier 411 regulates power to the motor and provides quadrature position feed back information signals. Torque transducer 412 measures the torque of the motor and is connected to torque signal unit 413 to provide a conditioned torque signal (both are provided by Sensor Development Corporation). 12 volt DC power supply 414 provides power for limit switches (not shown), ultrasonic distance sensor (not shown), and torque meter 412. The slide motor 415 is connected to turn slide jack screw 416 to control the vertical position of the upper clamp (see FIG. 21). Slide motor control box 417 regulates power for the slide motor. Ultrasonic sensor 418 (CONTAQ Technologies) measures the vertical position of the top clamp to determine the distance between the clamps for display on the operator's panel, and logging by the computer for each test. AC power is distributed by terminal blocks 420, 421.

Figure 24:
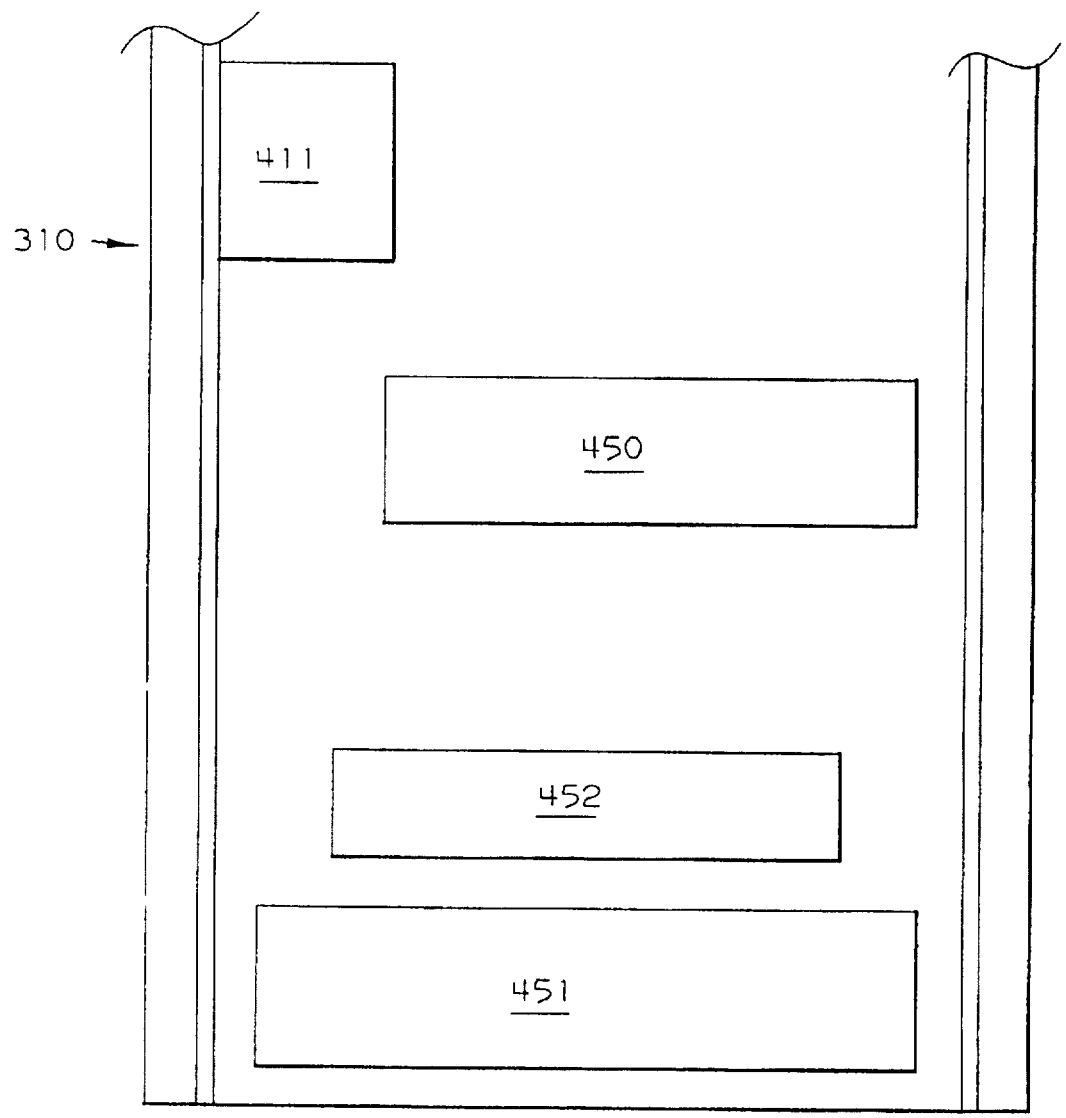
FIG. 24 is a rear view of the bottom section of the operator station of the tester of FIG. 15 with the back door removed.

FIG. 24 is a rear view of bottom section 310 of the main test station 304 with the back door (not shown) opened. The back end of drive motor amplifier 411 is seen at the top left of the drawing. Cable interface board connects the main station with any other stations in the machine. AC power box 451 provides for connection to AC power which is distributed to terminal blocks 420, 421 in FIG. 23. An AnaTech Test Circuit Monitor 452 is provided.

Although control of the machine and analysis could be provided purely by permanently configured hardware, it is convenient to provide a general purpose computer system which is configured during operation to provide the necessary apparatus to provide the required functions.

Figure 25:
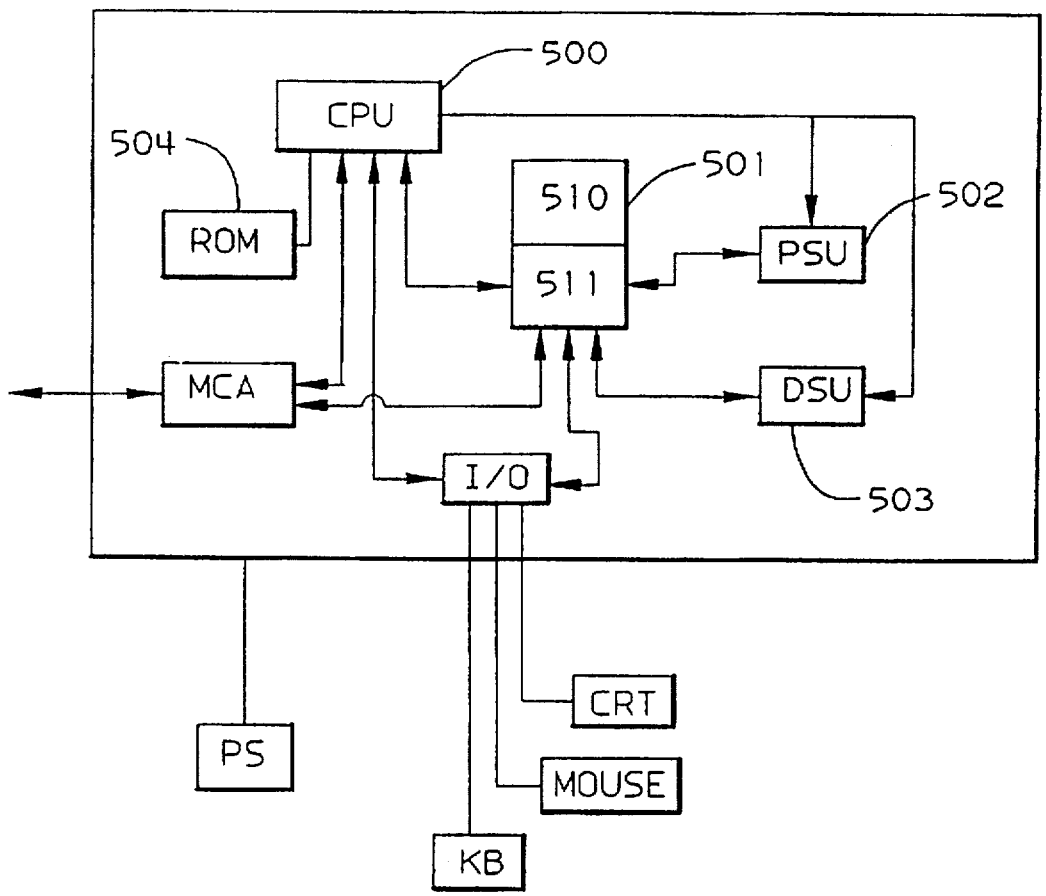
FIG. 25 is a schematic of the computer system of the operator station of the tester of FIG. 15.

As shown schematically in FIG. 25, the computer preferably includes a central processor unit (CPU) 500, random access memory (RAM) 501, a program storage unit (PSU) 502, a data storage unit (DSU) 503, and ROM 504 for initially transferring signals from the program storage unit to configure the RAM to proved various apparatus needed to control the CPU for controlling the machine during testing and analysis. The computer includes a motor control adapter (MCA) 505, such as an 8-axis Delta Tau PMAC-PC adapter, to control the various motors in the machine. The storage units include magnetic switches, optical switches, solid state switches or other machinery to cooperate with apparatus to generate signals to configure the RAM to provide apparatus required to control the CPU. The PSU and DSU storage devices can be combined if desired. During operation the RAM includes apparatus to present menus to the user and react to function keys, action bars, or mouse input (not shown). The RAM also includes control apparatus 510 to control the machine during testing and analysis apparatus 511 to perform the statistical analysis required of the system.

Figure 26:
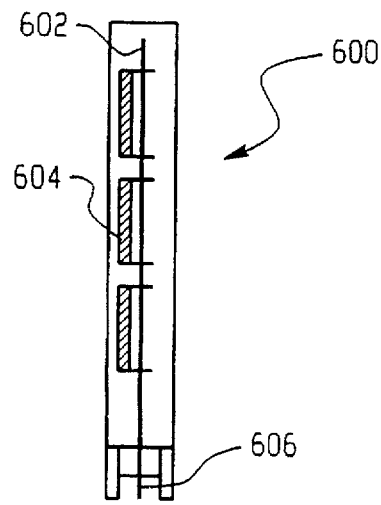
FIG. 26 is a schematic showing a solid state embodiment of the a signal generating system of the invention.

FIGS. 26–29 show examples of signal generating devices of the invention for controlling the operation of the torsion tester. FIG. 26, shows a program cartridge 600 such as a PCMCIA card which typically includes a circuit board 602 on which are mounted a discrete devices to generate signals or more preferably solid state memory devices 604 such as photo-lithographically programmed structures of a ROM chip or electrically programmed EPROM, EEPROM, bubble memory, battery backed SRAM, or flash memory chips. The devices are interconnected by a wiring layer (not shown) for example, on either surface of board 602. Programming may be used in a well known manner to provide the required functions in the memory or discrete circuits may be generated by a program. Connector 606 of the cartridge is inserted into a port or slot of the torsion tester for transmitting the signals which control the CPU of the tester. Alternately, the torsion tester may have a circuit board with sockets into which solid state memory devices are inserted.

Figure 27:
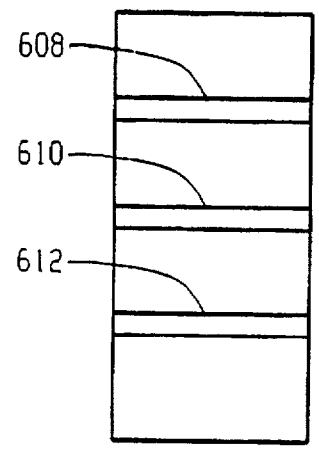
FIG. 27 is a schematic illustrating a map of the memory of the device in FIG. 26.

In FIG. 27, a memory map of the solid state memory devices includes separate apparatus sections 608, 610, 612 one or more of which carrying out one or more of the functions of the invention. For each of the generating device embodiments one or more of these sections provides one or more apparatus which include: apparatus for automatically counting the number of cycles during the torsion test; apparatus for receiving data for a multitude of failures for a circuit board; apparatus for relating the failure data to the number of cycles that have been counted prior to receiving the data to produce a distribution of failures by cycle; and apparatus for storing the failure distribution for later access. In addition for each generating device embodiment one or more of these sections preferably include one or more of: apparatus for automatically determining the angle to twist a card depending on input card size, thickness, and technology; apparatus for storing a predetermined termination failure count; apparatus for automatically terminating the torsion test depending on the termination failure count and the number of failures that have been received; apparatus for storing a predetermined termination cycle count; apparatus for automatically terminating the torsion test depending on the termination cycle count and the number of cycles that have been counted; apparatus for measuring the maximum angle of twist or the maximum torque for each torsion cycle and storing data related to the maximum angle or maximum torque; apparatus for identifying the process or technology for a failure distribution; apparatus for comparing failure distributions to identify anomalous differences; apparatus for generating an average failure distribution from a multitude of stored distributions for cards to form baseline or reference distributions of expected failures for a particular process and technology; apparatus for comparing failure distributions to identify anomalous differences; apparatus for generating an average failure distribution from a multitude of stored distributions for cards to form baseline or reference distributions of expected failures for a particular process and technology; apparatus for determining the reliability of cards made by a process by normalizing a distribution of fails for the card depending on a generated baseline distribution; apparatus for receiving failure signals from a circuit board as they occur during testing; apparatus for receiving a locations for failures; apparatus for relating the failure location to the number of cycles to produce a distribution for failures by location and cycle; storing the distribution with failure locations related to failure cycles; apparatus for storing failure distributions for a plurality of circuit boards.

Figure 28:
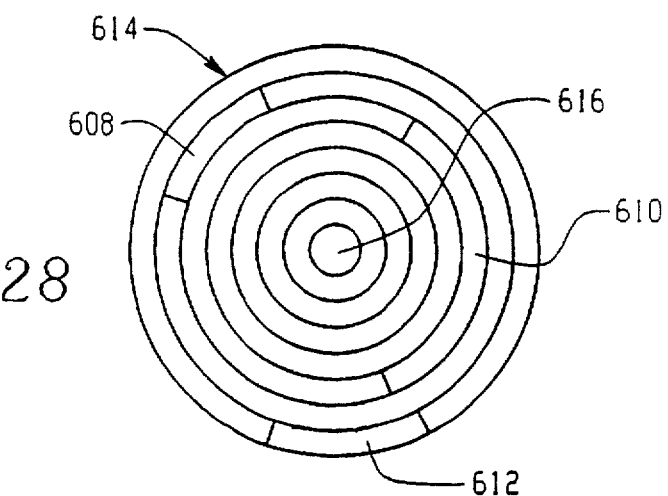
FIG. 28 is a schematic showing a floppy disk embodiment of a signal generating system of the invention.

FIG. 28 shows a disk 614 which may be a floppy plastic substrate such as a disk or a tape, covered by ferromagnetic particles which can be set by magnetically orienting the particles and used to generate digital signals when moved through a magnetic field. Alternately the magnetic particles may be on a card which is moved or swiped in relation to the magnetic field. Usually the magnetic field is generated by and read or read/write head and also the magnetic signals transduced into electrical signals in a read or read/write head of a disk drive as the disk spins about hole 616. More preferably the disk is coated by a medium with a reflectance which is controlled to provide radiation signals when a laser beam is directed to reflect off the surface as the disk spins about the center hole. Alternately the laser beam can be directed to scan over the surface of a fixed card. A detector of electromagnetic radiation transduce the optic signals to provide digital electrical signals. A spiral track or a plurality of round concentric tracks are divided up into apparatus sections such as 608, 610, 612 and one or more of the sections is used to provide one or more of the apparatus described above in relation to the solid state signal generating device of FIG. 27.

Figure 29:
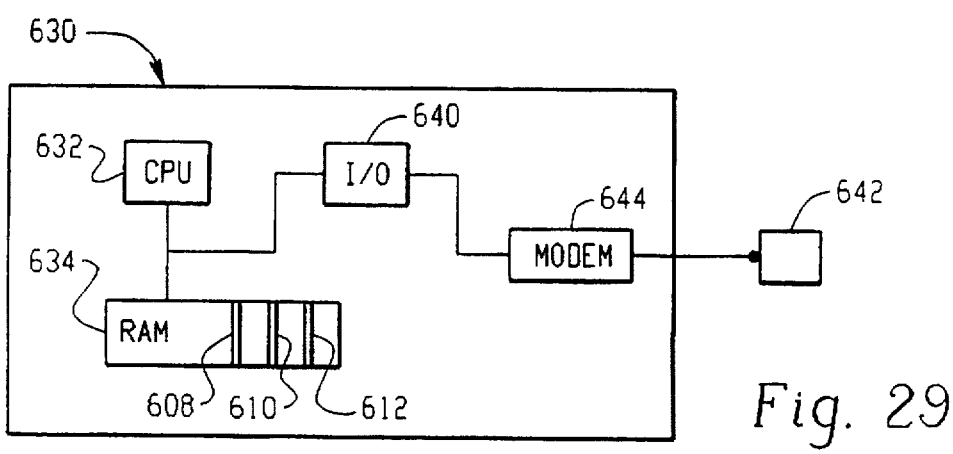
FIG. 29 is a schematic showing a computer system embodiment of a signal generating system of the invention.

FIG. 29 shows a computer system 630 with one or more CPU's 632 communicating with memory 634 (registers, SRAM, DRAM, and/or EEPROM) which contains apparatus sections 636 which are discrete circuits or more preferably transistor memory devices which have been configured for example by using a program to provide the desired apparatus sections 608, 610, 612 as described above for the solid state signal generating device of FIG. 27. The CPU(s) and memory 634 communicate with an input/output controller 640 to transmit signals onto an external communications network 642 to which the computer system of the operator station of FIG. 25 is connected (not shown). The network may be any type of network through which computer systems communicate. For a telephone network MODEM 644 is required to convert voltage level signals to frequency signals which are transmitted to a second MODEM (not shown) which is connected to the system of FIG. 25.

Although the invention has been described specifically in terms of preferred embodiments, such embodiments are provided only as examples. Those skilled in the art are expected to make numerous changes and substitutions including those discussed above, in arriving at their own embodiments without departing from the scope of the present invention and the following claims.

We claim:

1. A method for determining the quality of solder joints in electrical circuit assemblies having at least one component type thereon in a mechanical deflection system (MDS), the method comprising the steps of:

(a) commencing the cyclical torsion testing of a plurality of circuit assemblies;

(b) determining the location of any joint failures and the cycle at which they occurred in any of the plurality of circuit assemblies by monitoring the electrical resistance of at least one predetermined electrical joint in each of the plurality of circuit assemblies;

(c) generating fails scattering distributions based on circuit assembly component type, failed joint location, and component location on the circuit assembly;

(d) normalizing the fails scattering distributions based on a reference distribution selected from the fails scattering distributions, wherein this step comprises the step of determining a correlation factor;

(e) generating a mean MDS life based on the cycle and joint failure of each of the plurality of circuit assemblies; and (f) merging the normalized fails scattering distributions into an equivalent distribution that is indicative of the quality of the at least one predetermined electrical joint.

2. The method of claim 1 further comprising the step of comparing the reference distribution to each of the fails scattering distributions.

3. The method of claim 1 wherein the step of determining a correlation factor includes the step of calculating a correlation factor based on the following formula:

$$CF_i = \frac{(N_{50})_{reference}}{(N_{50})_i}$$

where $CF_i$ is the i-th distribution correlation factor, $(N_{50})_{reference}$ is the mean-life of fails distributions of the reference baseline and $(N_{50})_i$ is the mean-life of fails distributions for each of the i distributions.

4. The method of claim 1 further comprising the step of determining the mean MDS life and standard deviation of the equivalent distribution.

5. The method of claim 4 further comprising the step of outputting the mean MDS life and standard deviation of the equivalent distribution to an output device.

6. A method of monitoring circuit assembly, wherein the circuit includes at least one component type attached to a circuit board, the method comprising the steps of:

(a) generating a first baseline reference distribution from a stored database of mean mechanical deflection system (MDS) life and fails scattering distributions;

(b) selecting a plurality of circuit assemblies from an assembly line; and (c) applying cyclical torsion testing to the selected plurality of circuit assemblies to determine the presence of any anomalies in the circuit assembly line process, wherein this step comprises the steps of:

(1) commencing the cyclical torsion testing of the selected plurality of circuit assemblies;

(2) determining the location of any joint failures and the cycle at which they occurred in any of the selected plurality of circuit assemblies by monitoring the electrical resistance of at least one predetermined electrical joint in each of the selected plurality of circuit assemblies;

(3) generating fails scattering distributions based on circuit assembly component type, failed joint location, and component location on the circuit assembly;

(4) normalizing the fails scattering distributions based on a reference distribution selected from the fails scattering distributions;

(5) generating a mean MDS life based on the cycle and joint failure of each of the selected plurality of circuit assemblies, wherein this step comprises the step of determining a correlation factor;

(6) merging the normalized fails scattering distributions into a second baseline reference distribution; and (7) comparing the first and second reference baseline distributions to determine whether any anomalies are present.

7. The method of claim 6 further comprising the step of, if anomalies are determined in step (c) (7), generating a signal indicative of the presence of anomalies in the assembly line.

8. The method of claim 6 further comprising the step of, if no anomalies are determined in step (c) (7), merging the first and second reference baseline distributions into an enhanced baseline distribution.

9. The method of claim 6 wherein the step of determining a correlation factor includes the step of calculating a correlation factor based on the following formula:

$$CF_i = \frac{(N_{50})_{reference}}{(N_{50})_i}$$

where $CF_i$ is the i-th distribution correlation factor, $(N_{50})_{reference}$ is the mean-life of fails distributions of the reference baseline and $(N_{50})_i$ is the mean-life of fails distributions for each of the i distributions.

10. A system for determining the quality of solder joints in circuit assemblies having at least one component type thereon in a mechanical deflection system (MDS) the system comprising:

(a) means for applying cyclical torsion testing to circuit assemblies; and (b) a computer comprising:

(1) means for monitoring the electrical resistance of at least one predetermined electrical joint in each circuit assembly;

(2) logic for determining the location of any joint failures and the cycle at which they occurred in any of the circuit assemblies by monitoring the electrical resistance of the at least one predetermined electrical joint;

(3) logic for generating fails scattering distributions based on circuit assembly component type, failed joint location, and component location on the circuit assembly;

(4) logic for normalizing the fails scattering distributions based on a reference distribution selected from the fails scattering distributions;

(5) logic for generating a mean MDS life based on the cycle and joint failure of each of the plurality of circuit assemblies; and (6) logic for merging the normalized fails scattering distributions into an equivalent distribution that is indicative of the quality of the at least one predetermined electrical joint by determining a correlation factor.

11. The system of claim 10 wherein the logic for normalizing comprises logic for calculating a correlation factor based on the following formula:

$$CF_i = \frac{(N_{50})_{reference}}{(N_{50})_i}$$

where $CF_i$ is the i-th distribution correlation factor, $(N_{50})_{reference}$ is the mean-life of fails distributions of the reference baseline and $(N_{50})_i$ is the mean-life of fails distributions for each of the i distributions.

12. The system of claim 10 further comprising logic for determining the mean MDS life and standard deviation of the equivalent distribution.

* * * * *